United States Patent
Chong et al.

(10) Patent No.: US 11,090,309 B2
(45) Date of Patent: Aug. 17, 2021

(54) ANTI-THROMBOTIC AGENTS AND METHODS OF USE THEREOF

(71) Applicants: Temple University—Of The Commonwealth System of Higher Education, Philadelphia, PA (US); Molecular Targeting Technologies, Inc., West Chester, PA (US)

(72) Inventors: Parkson L-G Chong, Cherry Hill, NJ (US); Lawrence E. Goldfinger, Philadelphia, PA (US); Koon Y. Pak, Malvern, PA (US); Brian D. Gray, Exton, PA (US)

(73) Assignees: TEMPLE UNIVERSITY-OF THE COMMONWEALTH SYSTEM OF HIGHER EDUCATION, Philadelphia, PA (US); Molecular Targeting Technologies. Inc., West Chester, PA (US)

( * ) Notice: Subject to any disclaimer, the term of this patent is extended or adjusted under 35 U.S.C. 154(b) by 0 days.

(21) Appl. No.: 16/626,996

(22) PCT Filed: Jul. 2, 2018

(86) PCT No.: PCT/US2018/040551
§ 371 (c)(1),
(2) Date: Dec. 27, 2019

(87) PCT Pub. No.: WO2019/006445
PCT Pub. Date: Jan. 3, 2019

(65) Prior Publication Data
US 2020/0138828 A1    May 7, 2020

Related U.S. Application Data

(60) Provisional application No. 62/527,194, filed on Jun. 30, 2017.

(51) Int. Cl.
*A61K 31/555* (2006.01)
*A61P 7/02* (2006.01)
*A61K 9/127* (2006.01)
*A61K 45/06* (2006.01)

(52) U.S. Cl.
CPC .......... *A61K 31/555* (2013.01); *A61K 9/1272* (2013.01); *A61K 45/06* (2013.01); *A61P 7/02* (2018.01)

(58) Field of Classification Search
None
See application file for complete search history.

(56) References Cited

U.S. PATENT DOCUMENTS

| | | |
|---|---|---|
| 5,466,468 A | 11/1995 | Schneider |
| 7,179,616 B1 | 2/2007 | Smith |
| 7,354,581 B2 | 4/2008 | Cedarbaum |
| 2008/0171351 A1 | 7/2008 | Smith |
| 2016/0370360 A1 | 12/2016 | Belle |

FOREIGN PATENT DOCUMENTS

WO    2015179299 A1    11/2015

OTHER PUBLICATIONS

Ayesa et al., "Liposomes Containing Lipid-Soluble Zn(II)-Bis-dipicolylamine Derivatives Show Potential to Be Targeted to Phosphatidylserine on the Surface of Cancer Cells". Molecular Pharmaceutics, vol. 14, No. 1, Jan. 2017, published online Nov. 9, 2016, pp. 147-156.

Ayesa, U. "Archaeosomes and DPA-CY3[22,22]/POPC Liposomes and In Vitro Evaluation of Their Potential Usefulness in Targeted Delivery and Controlled Release" Ph.D. Dissertation submitted May 2016 (168 pages).

Clear, K.J., et al.; Bioconjug Chem. Feb. 17, 2016; 27(2): 363-375. Phenoxide-bridged Zinc(II)-Bis(dipicolylamine) Probes for Molecular Imaging of Cell Death.

Recognition of Anionic Cell Membranes using Targeted Liposomes Coated with Zinc(II)-bis(dipicolylamine) Affinity Units. Turkyilmaz, S.; Rice, D. R.; Palumbo, R.; Smith, B. D. Org. Biomol. Chem. 2014, 12, 5645-5655.

*Primary Examiner* — Brian J Davis
(74) *Attorney, Agent, or Firm* — Riverside Law LLP

(57) ABSTRACT

The present invention is related to compositions and methods for treating platelet-related diseases.

23 Claims, 7 Drawing Sheets

ANTI-THROMBOTIC AGENTS AND METHODS OF USE THEREOF

CROSS-REFERENCE TO RELATED APPLICATIONS

The present application is a 35 U.S.C. § 371 national phase application from, and claiming priority to, International Application No. PCT/US2018/040551, filed Jul. 2, 2018, which claims priority under 35 U.S.C. § 119(e) U.S. Provisional Patent Application No. 62/527,194, filed Jun. 30, 2017, all of which are incorporated herein by reference in their entireties.

BACKGROUND

Platelets are blood-borne cell fragments which monitor the blood vasculature for damage, whereupon platelets become rapidly activated resulting in platelet granule secretion and membrane rearrangements leading to localized recruitment and activation of coagulation factors, platelet crosslinking to fibrin, and generation and stabilization of a platelet-based clot (thrombus). Thrombus formation and stabilization are thus critical for hemostasis—maintenance of vascular blood flow and prevention of bleeding—but alternatively hyperactivity of platelets caused by many factors can result in increased risk for pathological thrombosis. Pathological thrombosis or thromboembolism causing blood vessel occlusion is the damaging and potentially deadly event in stroke and myocardial infarction, and often the major life-threatening risk event in patients with arteriosclerosis and atherosclerosis; hence, pathological thrombosis and thromboembolism remain the leading causes or morbidity and mortality worldwide. In addition, platelet-induced clotting must be prevented during vascular surgery, and moreover post-surgical complications often result as direct or indirect byproducts of platelet stimulation during surgical procedures.

Current anti-coagulants used clinically, primarily warfarin and heparin, have major clinical problems. Heparin treatment can cause heparin-induced thrombocytopenia as a result of antibodies against heparin-platelet factor 4 complexes, and warfarin treatment is well known to cause bleeding by globally inhibiting synthesis of essential clotting factors. Both of these complications can have serious immediate consequences but also cause long-term problems. Newer anti-coagulant drugs targeting coagulation factors, e.g., factor Xa inhibitors such as Xarelto (rivaroxaban), apixaban, edoxaban, and Pradaxa (dabigatran), have quick onset of action, but short half-lives, and require substantial dosage for acute effects.

While phosphatidylserine (PS) is normally maintained on the inner leaflet of mammalian cellular plasma membranes, cellular activation in some cells, as well as programmed cell death, causes surface exposure of PS to the outer leaflet. Upon platelet stimulation, PS is exposed on the outer leaflet of the plasma membrane, and the PS acts specifically as a docking site and activation stage for critical components of the coagulation cascade. PS exposure on platelets is required for thrombus formation and thrombus stabilization. This effect has been shown both through direct experimentation as well as in human disease and mouse models of disease, in which patients or animals with mutations in the platelet-specific genes required for PS exposure experience bleeding diathesis as a direct and selective result of lack of PS exposure on activated platelets. In addition, upon activation platelets release microvesicles, also known as microparticles (PMPs for platelet-derived microparticles), which bud from the platelet surfaces and have PS exposed. The PMPs also constitute critical mediators of thrombus formation and stability by enhancing the localized pro-coagulant surface area via increased localized PS concentration.

There is a need in the art for unique anti-thrombolytic agents. This invention addresses this unmet need.

SUMMARY OF THE INVENTION

In one aspect, the present invention relates to an anti-thrombolytic liposomal composition comprising: a phospholipid; and a compound of Formula (I);

FD-L-MBD          Formula (I);

wherein, in Formula (I), FD is a fluorescent domain which further comprises at least one hydrophobic group; L is a divalent linker; and MBD is a metal-binding domain. In one embodiment, MBD comprises $Cu^{2+}$, $Cu^+$, or $Zn^{2+}$. In one embodiment, MBD comprises $Zn^{2+}$. In one embodiment, MBD comprises di-(2-picolyl)amine.

In one embodiment, FD is represented by the following Formula (III)

Formula (III)

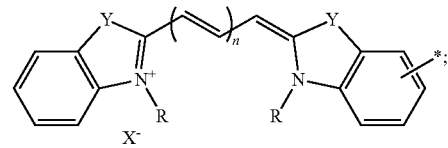

wherein Y is O, S, $Si(Me)_2$, or $C(Me_2)$; X is OH, Cl, I, Br, F, $ClO_4$, $NO_3$, or $CH_3C(O)O$; n is an integer selected from the group consisting of 1, 2, and 3; each of occurrence of R may be the same or different and represents a linear or branched $(C_1-C_{40})$alkyl group; and * represents the connection to divalent linking group L. In one embodiment, R is a linear $(C_{10}-C_{28})$alkyl group.

In one embodiment, the compound of Formula (I) is
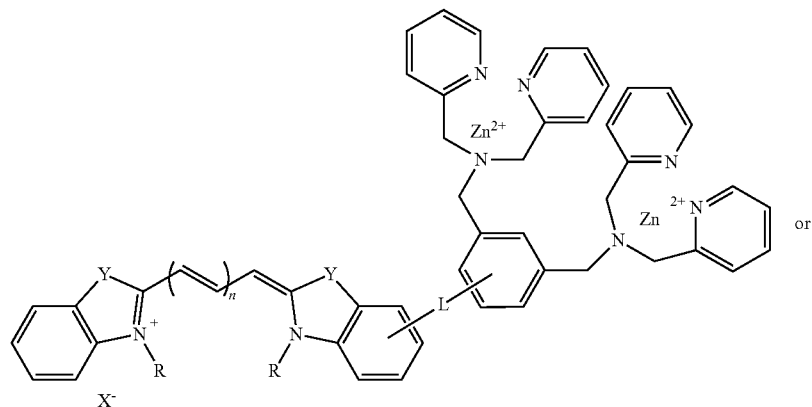
or
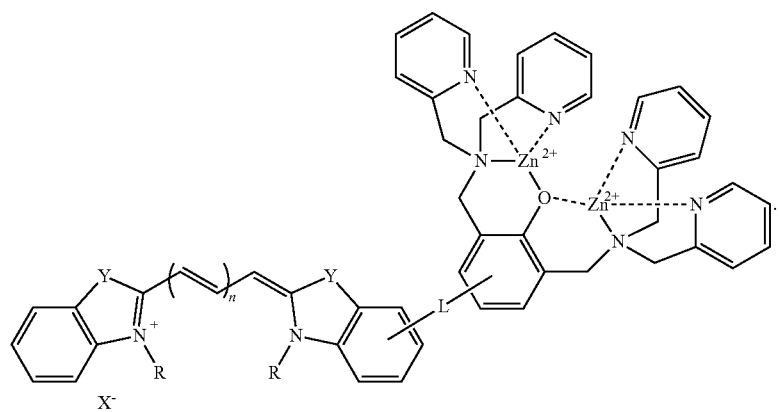
In one embodiment, the compound of Formula (I) is selected from the group consisting of
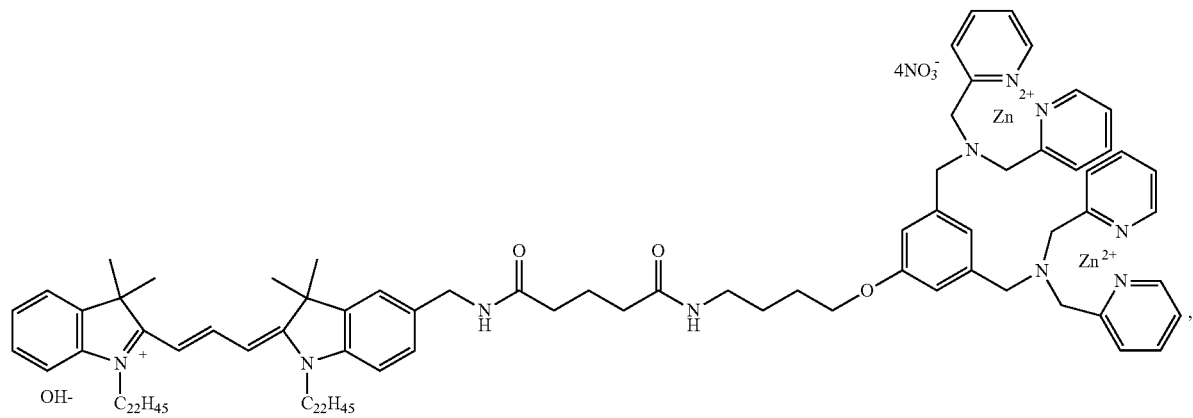
Zn(II) DPA-Cy3[22,22]

-continued
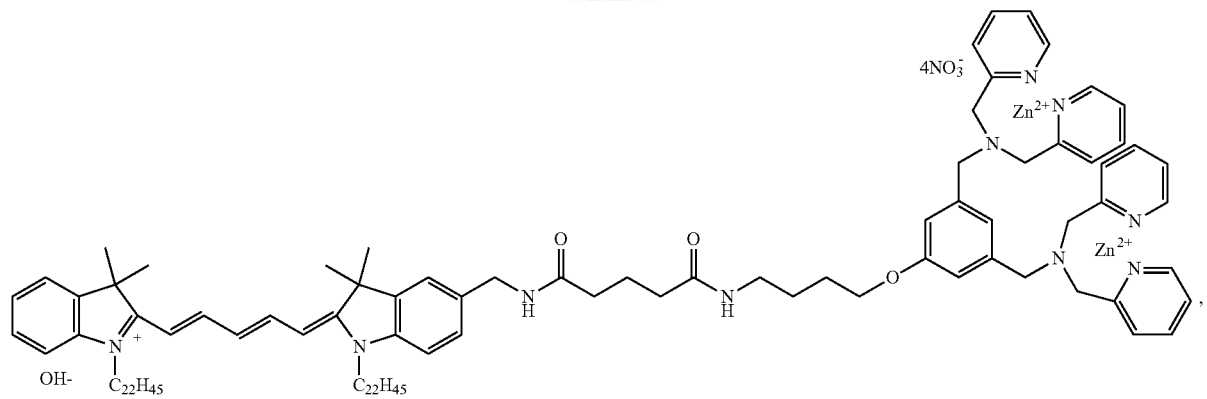
Zn(II) DPA-Cy5[22,22]
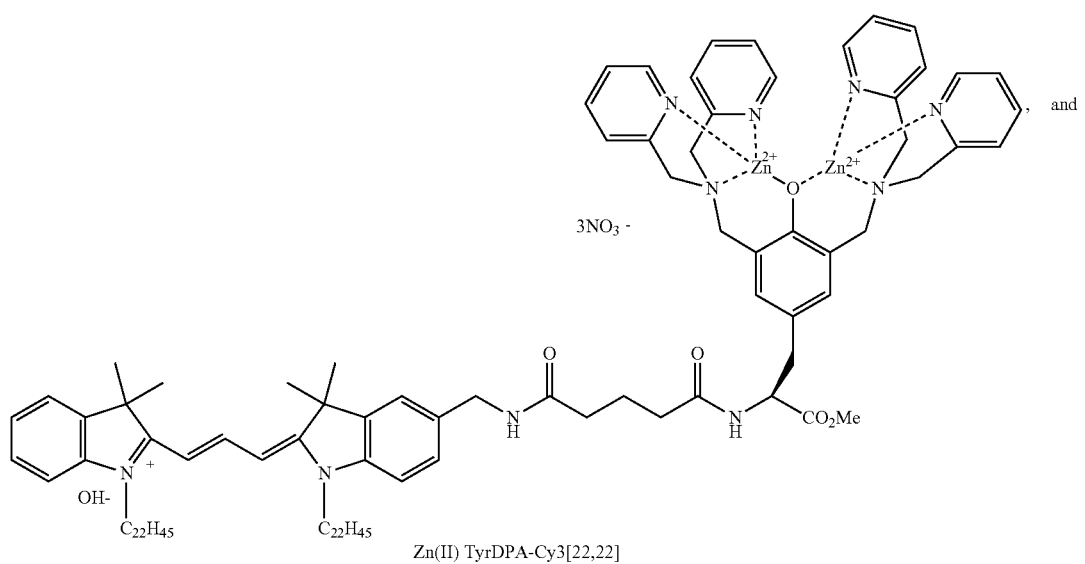
Zn(II) TyrDPA-Cy3[22,22]
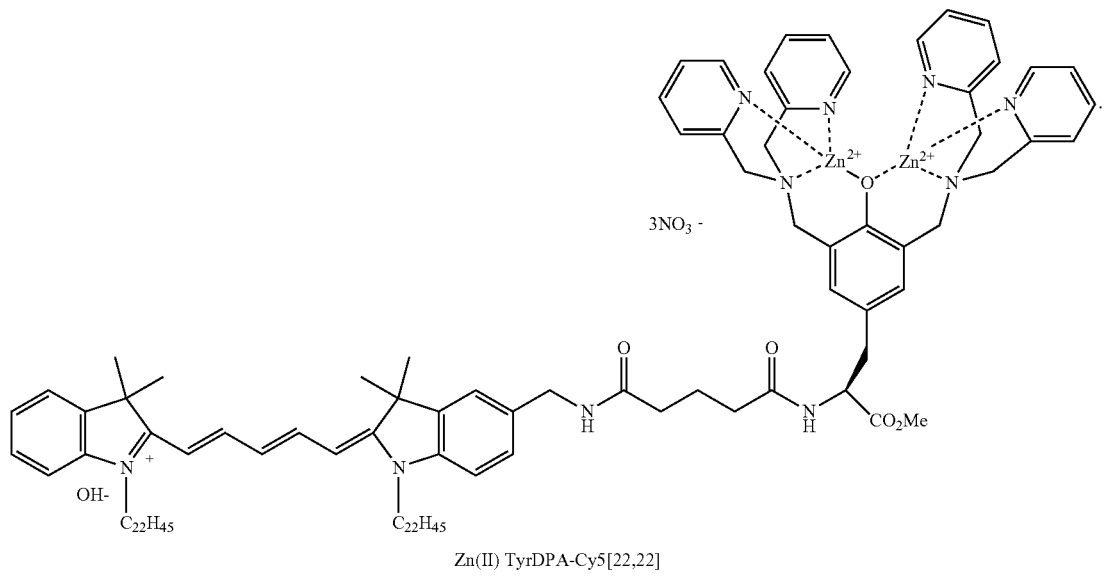
Zn(II) TyrDPA-Cy5[22,22]

In another aspect, the present invention relates to an anti-thrombolytic liposomal composition comprising: a phospholipid; and a compound of Formula (II);

$$(R')_2N-L'-MBD' \qquad \text{Formula (II);}$$

wherein, in Formula (II), R' is a linear or branched ($C_3$-$C_{28}$) alkyl group; L' is a divalent linker; and MBD' is a metal-binding domain. In one embodiment, the compound of Formula (II) is selected from the group consisting of

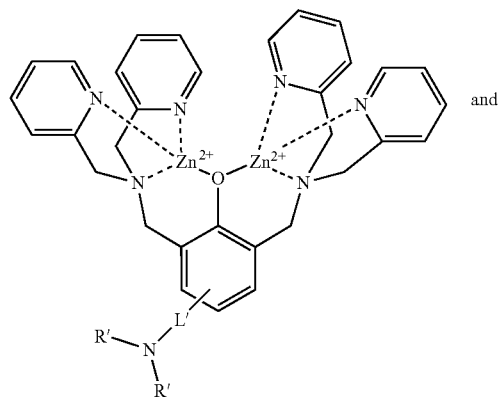

In one embodiment, the compound of Formula (II) is selected from the group consisting of

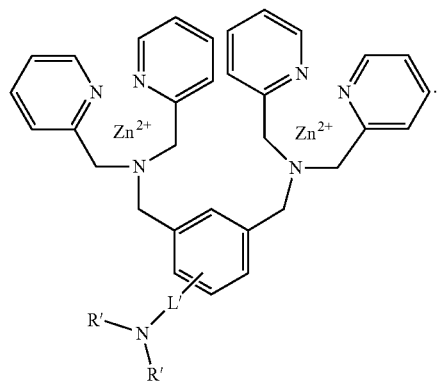

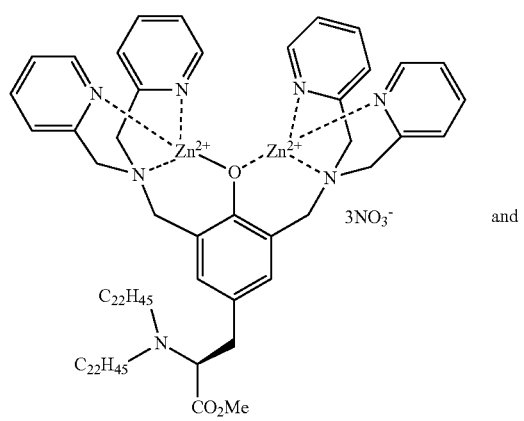

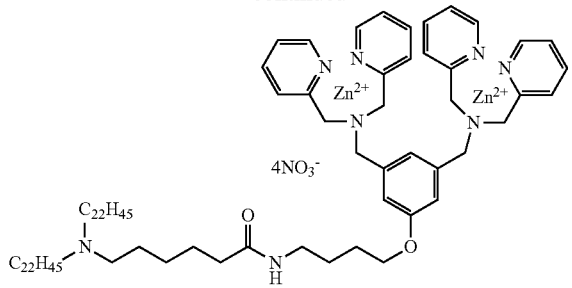

In one embodiment, the phospholipid is selected from the group consisting of a phosphatidylcholine, a lysophosphatidylcholine, a phosphatidic acid sodium salt, a phosphatidylglycerol, a phosphatidylserine, and a phosphatidylethanolamine. In one embodiment, the phospholipid is selected from the group consisting of 1,2-dipalmitoyl-sn-glycero-3-phosphocholine (DPPC), 1,2-dioleoyl-sn-glycero-3-phosphocholine (DOPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-palmitoyl-sn-glycero-3-phosphocholine (SPPC), and 1-myristoyl-2-palmitoyl-sn-glycero-3-phosphocholine (MPPC). In one embodiment, the phospholipid forms a vesicle selected from the group consisting of a liposome, a nanoliposome, a niosome, a microsphere, a nanosphere, a nanoparticle, a micelle, and an exosome. In one embodiment, the phospholipid forms a liposome with average diameter of between about 100 nm and 150 nm. In one embodiment, the vesicle is unilamellar. In one embodiment, the liposomal composition further comprises a chemotherapeutic agent. In one embodiment, the liposomal composition further comprises an antiplatelet agent, an adrenoceptor antagonist, a calcium channel blocker, or a vasodilator.

In another aspect, the present invention relates to a method of treating a platelet-related disease or disorder in a subject in need thereof, the method comprising the step of administering to the subject a liposomal composition of the present invention. In one embodiment, the platelet-related disease or disorder is selected from the group consisting of stroke, myocardial infarction, reperfusion injury, sepsis, clotting during surgery, deep vein thrombosis, thrombosis resulting from bypass surgery, stent implantation, and inflammation. The present invention relates in part to a method of treating or preventing thrombosis in a subject in need thereof, the method comprising the step of administering to the subject a liposomal composition of the present invention. The present invention also relates in part to a method of binding phosphatidylserine, the method comprising contacting phosphatidylserine with a liposomal composition of the present invention.

In one aspect, the present invention relates to a method of treating a platelet-related disease or disorder in a subject in need thereof, the method comprising the step of administering to the subject liposomes comprising a phospholipid and a compound selected the group consisting of

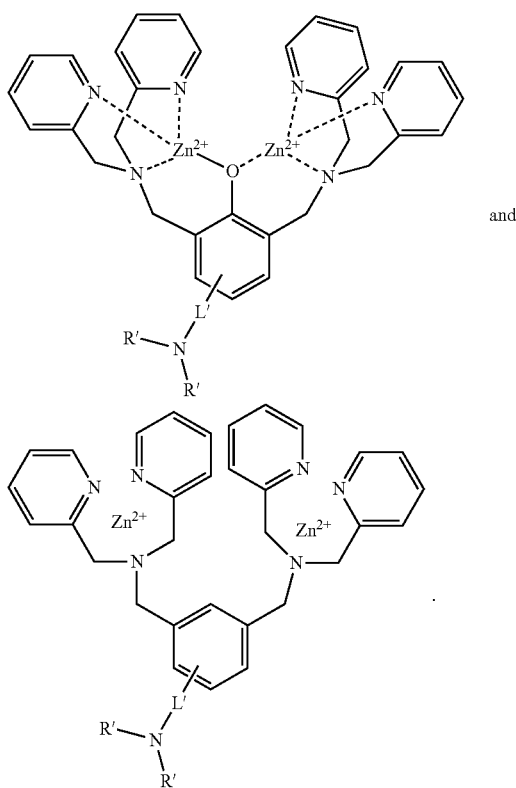

and wherein Y is O, S, Si(Me)$_2$, or C(Me$_2$); X is OH, Cl, I, Br, F, ClO$_4$, NO$_3$, or CH$_3$C(O)O; n is an integer selected from the group consisting of 1, 2, and 3; each of occurrence of R may be the same or different and represents a linear or branched (C$_1$-C$_{40}$)alkyl group; and L is a divalent linker.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1:
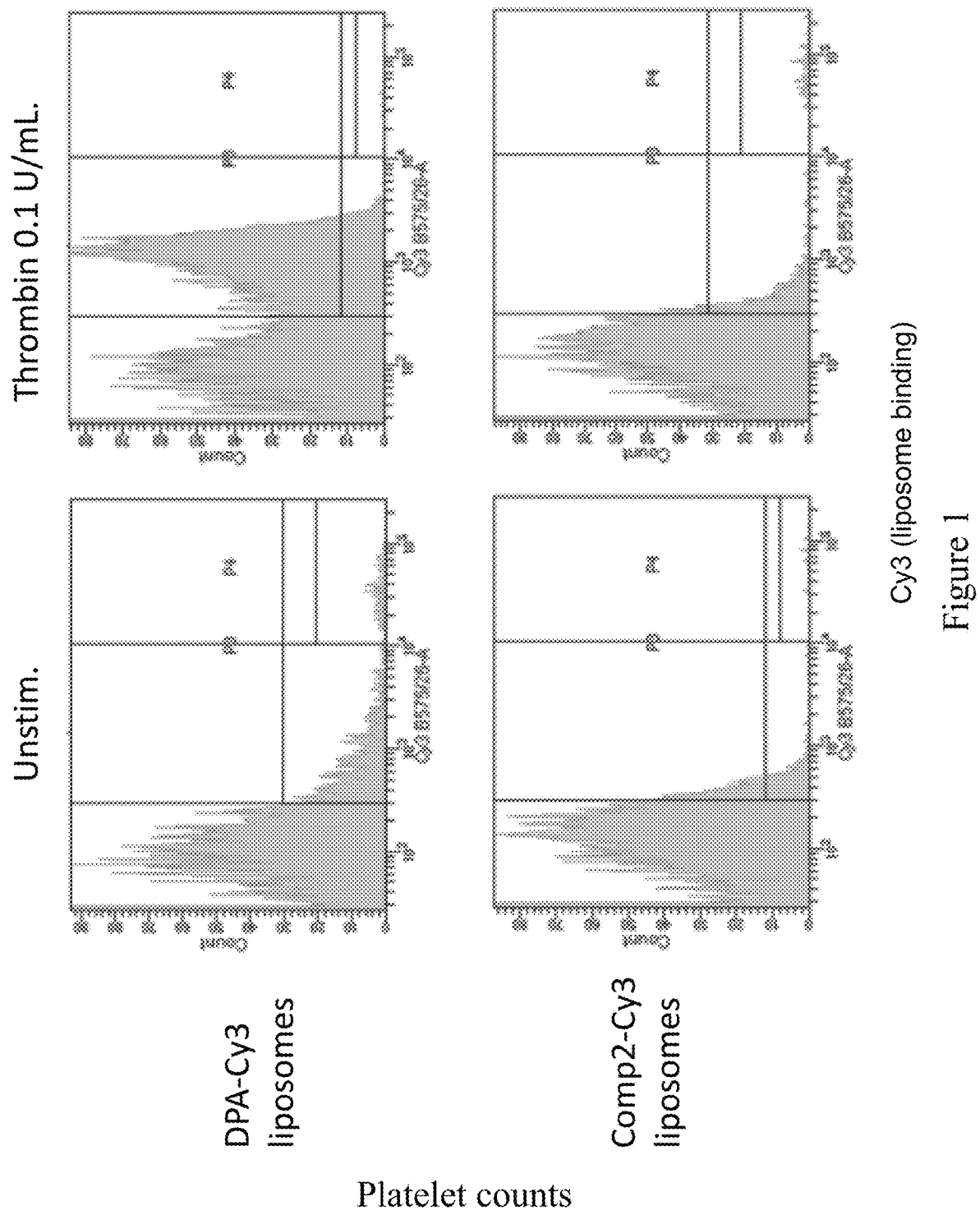
FIG. 1, depicts the results of example experiment demonstrating specific binding of DPA-Cy3 liposomes to activated platelets. Freshly isolated human platelets were incubated with 5 µl of the indicated liposome formulations and treated with the indicated agonists at 37° C. for 10 minutes, fixed, washed and analyzed by flow cytometry for Cy3 fluorescence. Abscissa, Cy3 fluorescence intensity, a.u.; ordinate, event counts.
Figure 1:
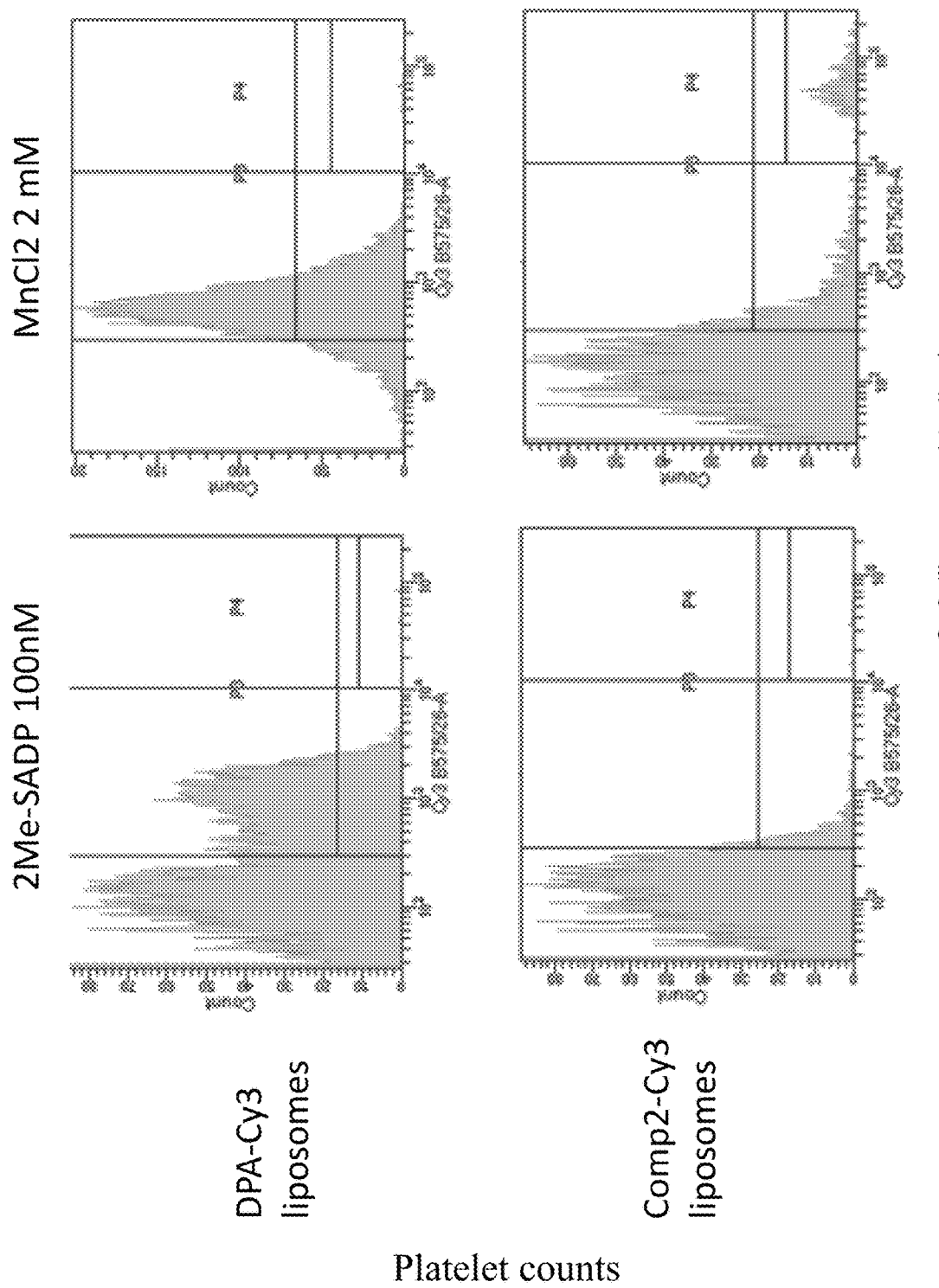

The present invention relates in part to the discovery that that DPA-Cy3[22,22]/POPC liposomes selectively bind activated platelets and PMPs, blocking PS sites and preventing coagulation, and thus act as an anti-thrombotic agent in vivo. In one embodiment, the purpose of this invention is to act as a blood-borne anti-thrombotic agent for acute treatment in multiple clinical scenarios, and potentially with prophylactic applications.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human. As used herein, a subject is preferably a mammal such as a non-primate (e.g., cows, pigs, horses, cats, dogs, rats, etc.) and a primate (e.g., monkey and human), most preferably a human.

"Parenteral" administration of a composition includes, e.g., subcutaneous (s.c.), intravenous (i.v.), intramuscular (i.m.), or intrasternal injection, or infusion techniques.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

To "treat" a disease as the term is used herein, means to reduce the frequency or severity of at least one sign or symptom of a disease or disorder experienced by a subject.

As used herein, the term "attached to" refers to attaching two chemical groups through a chemical bond, for example a covalent bond or a non-covalent bond.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Other examples include ($C_1$-$C_6$)alkyl, such as, but not limited to, ethyl, methyl, isopropyl, isobutyl, n-pentyl, n-hexyl and cyclopropylmethyl. Similarly, $C_{22}$alkyl means a straight or branched chain hydrocarbon having 22 carbon atoms.

As used herein, the term "cycloalkyl" refers to a mono cyclic or polycyclic non-aromatic group, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

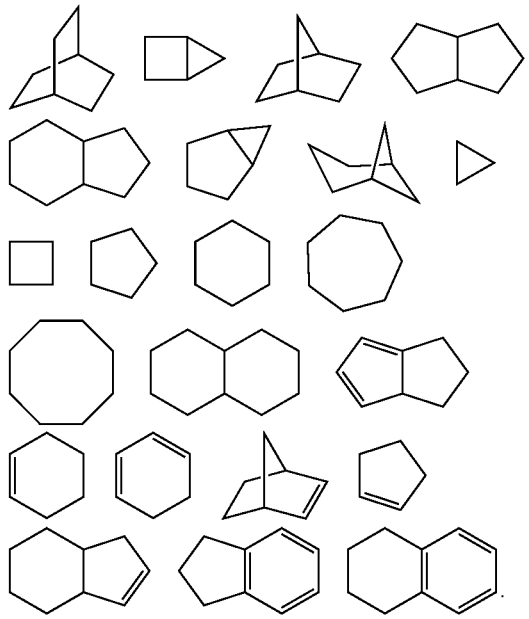

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon-carbon double bond or one carbon-carbon triple bond.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—$CH$=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents. In one embodiment, the substituents are selected from the group consisting of halogen, —OH, alkoxy, tetrahydro-2-H-pyranyl, —NH$_2$, —N(CH$_3$)$_2$, (1-methyl-imidazol-2-yl), pyridin-2-yl, pyridin-3-yl, pyridin-4-yl, —C(=O)OH, trifluoromethyl, —C≡N, —C(=O)O(C$_1$-C$_4$)alkyl, —C(=O)NH$_2$, —C(=O)NH(C$_1$-C$_4$)alkyl, —C(=O)N((C$_1$-C$_4$)alkyl)$_2$, —SO$_2$NH$_2$, —C(=NH)NH$_2$, and —NO$_2$, In one embodiment, one or two substituents are present and include halogen, —OH, alkoxy, —NH$_2$, trifluoromethyl, —N(CH$_3$)$_2$, and —C(=O)OH. In one embodiment, the substituents include halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Non-limiting examples include (C$_1$-C$_3$)alkoxy, such as, but not limited to, ethoxy and methoxy.

As used herein, the term "halo" or "halogen" alone or as part of another substituent means, unless otherwise stated, a fluorine, chlorine, bromine, or iodine atom. In one embodiment, halo includes fluorine, chlorine, or bromine. In one embodiment, halo includes fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of B, O, N, S, and P and wherein the nitrogen, sulfur, and phosphorous atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of B, O, N, S, and P and wherein the nitrogen, sulfur, and phosphorous atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

As used herein, the term "aromatic" refers to a carbocycle or heterocycle with one or more polyunsaturated rings and having aromatic character, i.e., having (4n+2) delocalized p (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. In one embodiment, aryl includes phenyl and naphthyl. In one embodiment, the aryl is phenyl.

As used herein, the term "aryl-(C$_1$-C$_3$)alkyl" or "arylalkyl" means a functional group wherein a one to three carbon alkylene chain is attached to an aryl group, e.g., —CH$_2$CH$_2$-phenyl or —CH$_2$-phenyl (benzyl). Preferred is aryl-CH$_2$— and aryl-CH(CH$_3$)—. The term "substituted aryl-(C$_1$-C$_3$) alkyl" means an aryl-(C$_1$-C$_3$)alkyl functional group in which the aryl group is substituted. In one embodiment, the aryl-alkyl is substituted aryl(CH$_2$)—. Similarly, the term "heteroaryl-(C$_1$-C$_3$)alkyl" means a functional group wherein a one to three carbon alkylene chain is attached to a heteroaryl group, e.g., —CH$_2$CH$_2$-pyridyl. In one embodiment, the heteroaryl-(C$_1$-C$_3$)alkyl is heteroaryl-(CH$_2$)—. The term "substituted heteroaryl-(C$_1$-C$_3$)alkyl" means a heteroaryl-(C$_1$-C$_3$)alkyl functional group in which the heteroaryl group is substituted. In one embodiment, the substituted heteroaryl-(C$_1$-C$_3$)alkyl is substituted heteroaryl-(CH$_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of B, O, N, S, and P and wherein the nitrogen, sulfur, and phosphorous heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl. A polycyclic heteroaryl may include one or more rings that are partially saturated. Examples include the following moieties:

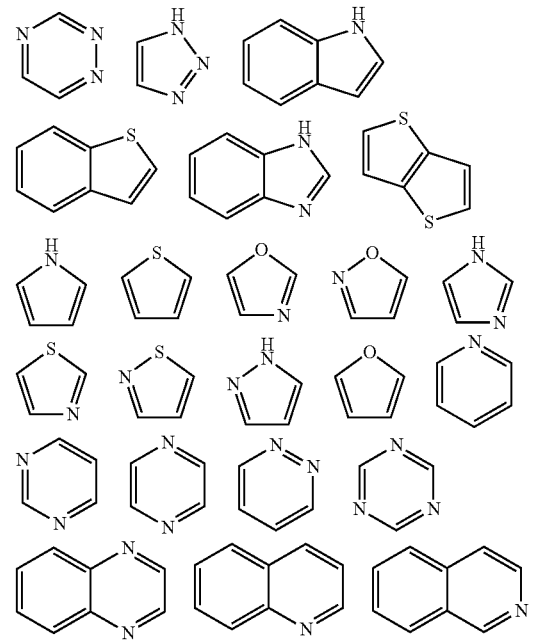

-continued

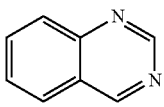

As used herein, the term "heterocycloalkyl" or "heterocyclyl" refers to a heteroalicyclic group containing one to four ring heteroatoms each selected from B, O, S, N, and P. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

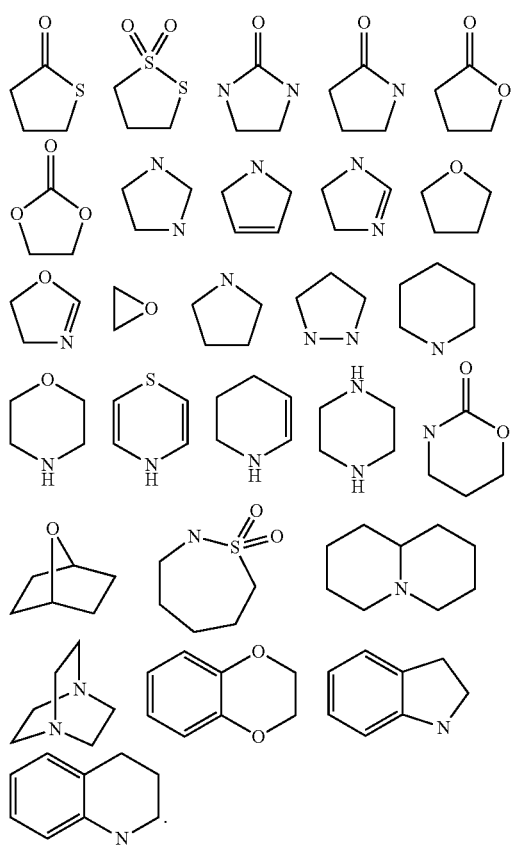

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "heteroaryl" or "heteroaromatic" refers to a heterocycle having aromatic character. A polycyclic heteroaryl may include one or more rings that are partially saturated. Examples include the following moieties:

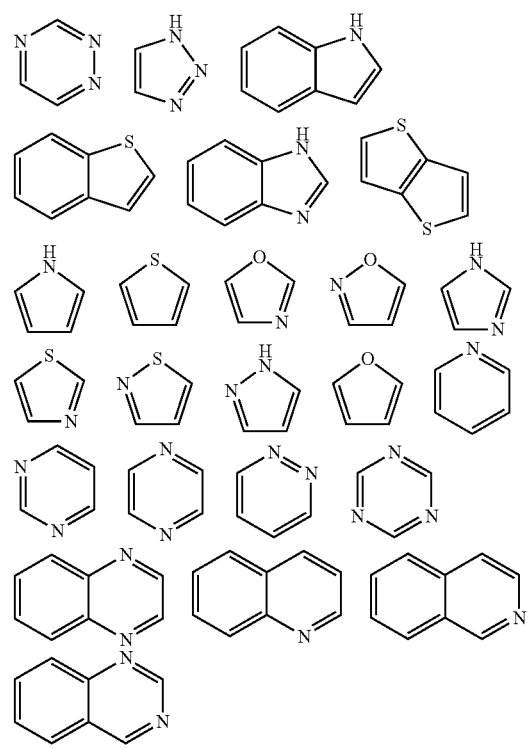

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In one embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —SO$_3$H, —C(=O)NH$_2$, —C(=O)—NHCH$_3$, —NHC(=O)NHCH$_3$, —C(=O)CH$_3$, and —C(=O)OH. In one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred. In one embodiment, the substituents are positively or negatively charged groups consisting of —NR$_3^+$, —SO$_3$—, or related species.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In one embodiment, the substituents vary in number between one and three. In one embodiment, the substituents vary in number between one and two.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates in part to the unexpected discovery of liposomal formulations with anti-thrombotic activity.

Compositions of the Invention

The compounds of the present invention may be synthesized using techniques well-known in the art of organic synthesis. The starting materials and intermediates required for the synthesis may be obtained from commercial sources or synthesized according to methods known to those skilled in the art.

In one aspect, the present invention relates to an anti-thrombolytic liposomal composition comprising: a phospholipid; and a compound of Formula (I);

FD-L-MBD;                                      Formula (I)

wherein, in Formula (I), FD is a fluorescent domain which further comprises at least one hydrophobic group; L is a divalent linker; and MBD is a metal-binding domain.

In another aspect, the present invention relates to an anti-thrombolytic liposomal composition comprising: a phospholipid; and a compound of Formula (II);

(R')$_2$N-L'-MBD'                              Formula (II);

wherein, in Formula (II), R' is a linear or branched (C$_1$-C$_{40}$) alkyl group; L' is a divalent linker; and MBD' is a metal-binding domain.

In one embodiment, metal-binding domain MBD is a group that binds a metal. In one embodiment, MBD comprises a metal. In one embodiment, MBD comprises a neutral metal atom. In one embodiment, MBD comprises a metal ion. Exemplary metals include, but are not limited to, Li, Na, K, Sc, Ti, V, Cr, Mn, Fe, Co, Ni, Cu, Zn, and cations or salts thereof. In one embodiment, MBD comprises Cu$^{2+}$, Cu$^+$, or Zn$^{2+}$.

In one embodiment, metal-binding domain MBD' is a group that binds a metal. In one embodiment, MBD' comprises a metal. In one embodiment, MBD' comprises a neutral metal atom. In one embodiment, MBD' comprises a metal ion. Exemplary metals include, but are not limited to, Li, Na, K, Sc, Ti, V, Cr, Mn, Fe, Co, Ni, Cu, Zn, and cations or salts thereof. In one embodiment, MBD' comprises Cu$^{2+}$, Cu$^+$, or Zn$^{2+}$.

In one embodiment, MBD comprises a metal chelator. In one embodiment, MBD comprises at least two metal chelators. In the case where MBD comprises more than one metal chelator, the metal chelators may be the same or different. In one embodiment, a metal chelator is considered to be a group that reversibly or irreversibly binds a metal or a metal ion. In one embodiment, MBD' comprises a metal chelator. In one embodiment, MBD' comprises at least two metal chelators. In the case where MBD' comprises more than one metal chelator, the metal chelators may be the same or different. In one embodiment, a metal chelator is considered to be a group that reversibly or irreversibly binds a metal or a metal ion.

Exemplary metal chelators include, but are not limited to, di-(2-picolyl)amine (DPA); bis(dipicolylamine) (BDPA); L-tyrosine-bis(dipicolylamine) (TyrBDPA); ethylenediaminetetra-acetic acid (EDTA); 1,3-diaminopropane-N,N,N',N'-tetraacetic acid (DTPA); N,N,N',N'-tetrakis(2-pyridylmethyl) ethylenediamine (TPEN); 1,10-phenanthroline; clioquinol; diethyldithiocarbamate (DEDTC), 2,3-dimercapto-1-propanesulfonic acid (DMPS); ethylenediamine-N,N'-diacetic-N,N'-di-B-propionic acid (EDPA); 1,2-dimethyl-3-hydroxy-4-pyridinone (DMHP); 1,2-diethyl-3-hydroxy-4-pyridinone (DEHP); ethyl maltol (EM), 4-(6-methoxy-8-quinaldinyl-aminosulfonyl)benzoic acid potassium salt (TFLZn); dithizone; N-(6-methoxy-8-quinolyl)-para-toluenesulfonamide (TSQ); carnosine; deferasirox; trans-1,2-cyclohexane-diamine-N,N,N',N'-tetraacetic acid (CyDTA); dihydroxyethylglycine (DHEG); 1,3-diamino-2-hydroxypropane-N,N,N',N'-tetraacetic (DTPA-OH); ethylenediamine-N,N'-diacetic acid (EDDA); ethylenediamine-N,N'-dipropionic acid (EDDP); ethylenediamine-N,N'-bis(methylphosphonic) acid (EDDPO); N-hydroxyethylenediamine-N,N',N'-triacetic acid (EDTA-OH); ethylenediaminetetra(methylenephosphonic) acid (EDTPO); N,N'-bis(2-hydroxybenzyl)ethylenediamine-N,N'-diacetic acid (HBED); hexamethylene-1,6-diaminetetraacetic acid (HDTA); hydroxyethyliminodiacetic acid (HIDA); iminodiacetic acid (IDA); methyl-EDTA, nitrilotriacetic acid (NTA); nitrilotripropionic acid (NTP), nitrilotrimethylenphosphonic acid (NTPO); O-BISTREN; triethylenetetramine hexaacetic acid (TTHA); ethylene glycol bis(2-aminoethyl ether)-N,N,N',N'-tetraacetic acid (EGTA); dimercaptosuccinic acid (DMSA); deferoxamine; dimercaprol; zinc citrate; combinations of bismuth and citrate; penicillamine; succimer; etidronate; ethylenediamine-di (O-hydroxyphenylacetic acid) (EDDHA); trans-1,2-cyclohexanediamine tetraacetic acid (CDTA); N-(2-hydroxyethyl) ethylenedinitrilotriacetic acid (HEDTA); N-(2-hydroxyethyl) iminodiacetic acid (HEIDA); 9-(O-carboxyphenyl)-2,7-dichloro-4,5,-bis[bis(2-pyridylmethyl)-aminomethyl]-6-hydroxy-3-xanthone; 9-(O-carboxyphenyl)-4,5-bis[bis(2-pyridylmethyl)-amino=omethyl]-6-hydroxy-3-xaritlianone; 9-(O-carboxyphenyl-2-chloro-5-[2-{bis(2-pyridylmethyl)aminomethyl}-N-methylaniline]-6-hydroxy-3-xanthanon calprotectin; zinc fingers; lactoferrin; ovotransferrin; conalbumin; salts thereof; and combinations thereof. In one embodiment, MBD comprises di-(2-picolyl) amine (DPA). In one embodiment, MBD comprises bis(dipicolylamine).

Divalent linking group L comprises any of a variety of compounds that can form an amide, ester, ether, thioether, carbamate, urea, amine or other linkage, e.g., linkages that are commonly used for immobilization of biomolecules in affinity chromatography. Divalent linking group L may comprise any alkyl chain, polyether chain, or polymer chain. In some embodiments, linking group L comprises a cleavable bond, e.g. a bond that is unstable and/or is cleaved upon changes in certain environmental parameters (e.g., pH or redox potential) or upon exposure to certain reagents, chemicals, catalysts, or enzymes. In some embodiments, linking group L is non-cleavable. In certain embodiments, linking group L is attached to MBD by one or more covalent bonds. In some embodiments, the linking group L is attached to FD through one or more covalent bonds.

Divalent linking group L' comprises any of a variety of compounds that can form an amide, ester, ether, thioether, carbamate, urea, amine or other linkage, e.g., linkages that are commonly used for immobilization of biomolecules in affinity chromatography. Divalent linking group L' may comprise any alkyl chain, polyether chain, or polymer chain. In some embodiments, linking group L' comprises a cleavable bond, e.g. a bond that is unstable and/or is cleaved upon changes in certain intracellular parameters (e.g., pH or redox potential). In some embodiments, linking group L' is non-cleavable. In certain embodiments, linking group L' is attached to MBD by one or more covalent bonds. In some embodiments, the linking group L' is attached to $N(R')_2$ through one or more covalent bonds.

In one embodiment, R' is $(C_1-C_{40})$alkyl. In one embodiment, R' is $(C_3-C_{28})$alkyl. In one embodiment, R' is $(C_{10}-C_{28})$alkyl. In one embodiment, R' is $C_3$alkyl. In one embodiment, R' is $C_2$alkyl. In one embodiment, R' is $C_3$alkyl. In one embodiment, R' is $C_7$alkyl. In one embodiment, R' is $C_6$alkyl. In one embodiment, R' is $C_3$alkyl. In one embodiment, R' is $C_{10}$alkyl. In one embodiment, R' is $C_{12}$alkyl. In one embodiment, R' is $C_{14}$alkyl. In one embodiment, R' is $C_{18}$alkyl. In one embodiment, R' is $C_{20}$alkyl. In one embodiment, R' is $C_{22}$alkyl. In one embodiment, R' is $C_{28}$alkyl.

In one embodiment, fluorescent domain FD comprises a synthetic dye. In one embodiment, FD comprises a fluorescent dye. In one embodiment, FD comprises a fluorophore. In one embodiment, FD comprises a cyanine dye. In one embodiment, cyanine dyes give strong fluorescence, providing a powerful tool for monitoring the locations and behaviors of the liposomes in vitro and in vivo research. In one embodiment, FD comprises a group of Formula (III).

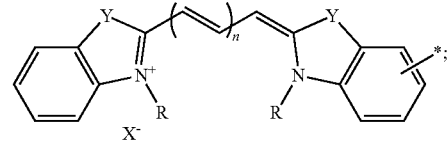

Formula (III)

wherein Y is O, S, $Si(Me)_2$, or $C(Me)_2$;
X is OH, Cl, I, Br, F, $ClO_4$, $NO_3$, or $CH_3C(O)O$;
n is an integer selected from the group consisting of 1, 2, or 3;
each of occurrence of R may be the same or different and represents a linear or branched $(C_1-C_{40})$alkyl group; and
* represents the connection to divalent linking group L.

In one embodiment, Y is $C(Me)_2$. In one embodiment, Y is O. In one embodiment, X is OH, Cl, I, or $ClO_4$. In one embodiment, n is 1. In one embodiment, n is 2.

In one embodiment, R is $(C_1-C_{40})$alkyl. In one embodiment, R is $(C_3-C_{28})$alkyl. In one embodiment, R is $(C_{10}-C_{28})$alkyl. In one embodiment, R is $C_3$alkyl. In one embodiment, R is $C_2$alkyl. In one embodiment, R is $C_3$alkyl. In one embodiment, R is $C_7$alkyl. In one embodiment, R is $C_6$alkyl. In one embodiment, R is $C_3$alkyl. In one embodiment, R is $C_{10}$alkyl. In one embodiment, R is $C_{12}$alkyl. In one embodiment, R is $C_{14}$alkyl. In one embodiment, R is $C_{18}$alkyl. In one embodiment, R is $C_{20}$alkyl. In one embodiment, R is $C_{22}$alkyl. In one embodiment, R is $C_{28}$alkyl.

In some embodiments, MBD is chemically tethered to FD by any suitable chemical conjugation technique. In some embodiments, the compound of Formula (I) is formed by conjugation of MBD with one valence of the linking group and by conjugation of FD with the other valence of the linking group. The linking group 1 between MDB and FD described herein is optionally non-cleavable or cleavable.

In some embodiments, linking group L comprises a cleavable bond. In other instances, linking group L is non-cleavable (i.e., does not comprise cleavable bonds). In certain non-limiting examples, the cleavable bonds include disulfide bonds (e.g., disulfide bonds that dissociate in certain reducing environments), ester bonds (e.g., lactide), a bond that is cleavable in acidic pH (e.g., endosomal conditions or within resorption pits), a bond that is cleavable by a specific enzyme (e.g., a phosphatase, or a protease a bond that is cleavable upon a change in an intracellular or extracellular parameter (e.g., pH, redox potential).

In some embodiments, covalent association between MBD and FD via linking group L is achieved through any suitable chemical conjugation method, including but not limited to amine-carboxyl linkers, amine-aldehyde linkers, amine-ketone linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, hydroxyl-hydroxyl linkers, and combinations thereof. In some embodiments, linking group L may further comprise spacing alkyl groups between linkers. In some embodiments, a bifunctional cross-linking reagent is employed to achieve the covalent conjugation between suitable conjugatable groups of MBD and FD. In some embodiments, conjugation is also performed with pH-sensitive bonds and linkers, including, but not limited to, hydrazone and acetal linkages. Any other suitable conjugation method is optionally utilized as well, for example a large variety of conjugation chemistries are available (see, for example, Bioconjugation, Aslam and Dent, Eds, Macmillan, 1998 and chapters therein).

In some embodiments, the compound of Formula (I) is selected from the group consisting of:

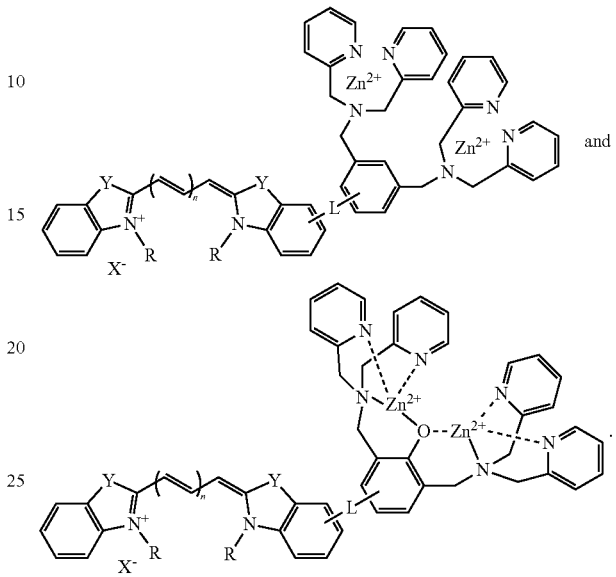

and

In one embodiment, the compound of Formula (I) is selected from the group consisting of

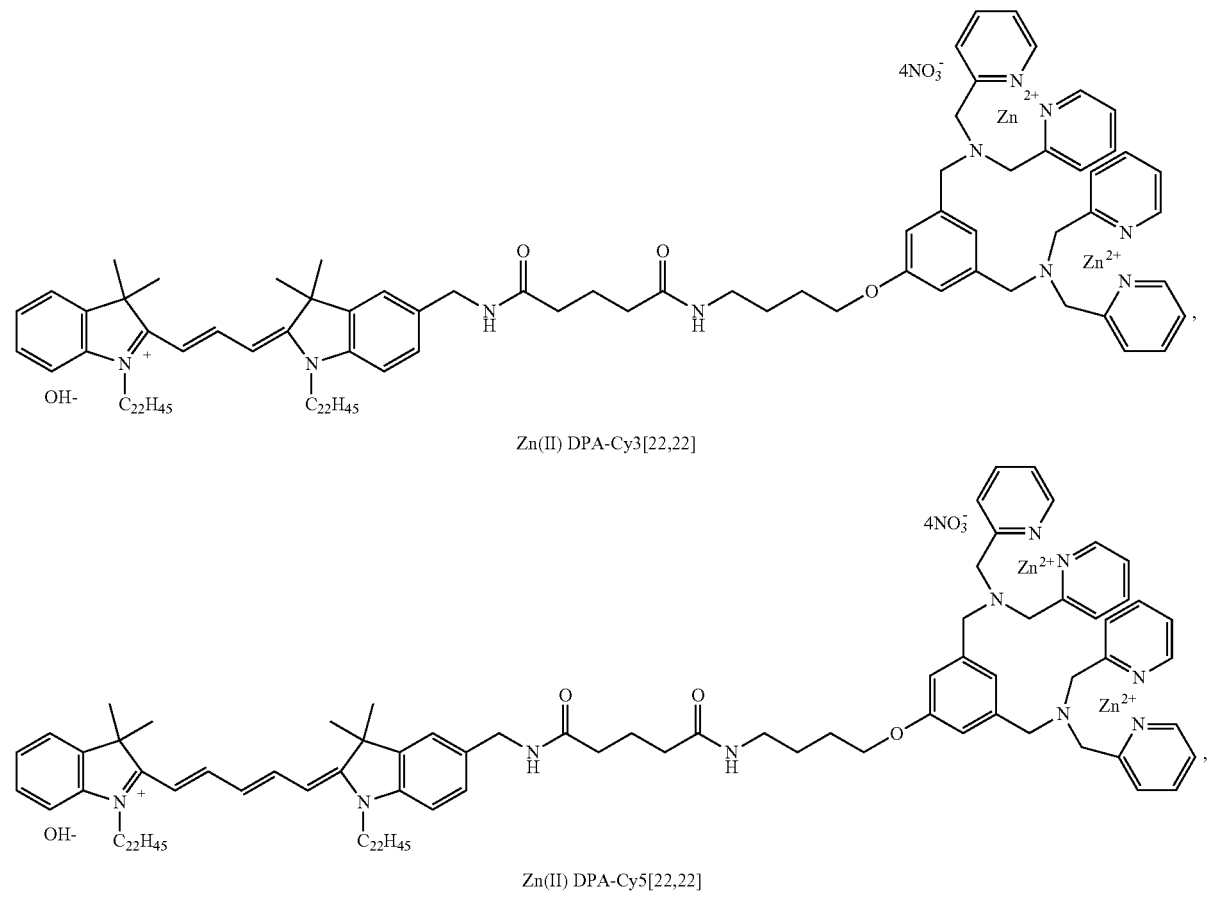

Zn(II) DPA-Cy3[22,22]

Zn(II) DPA-Cy5[22,22]

-continued
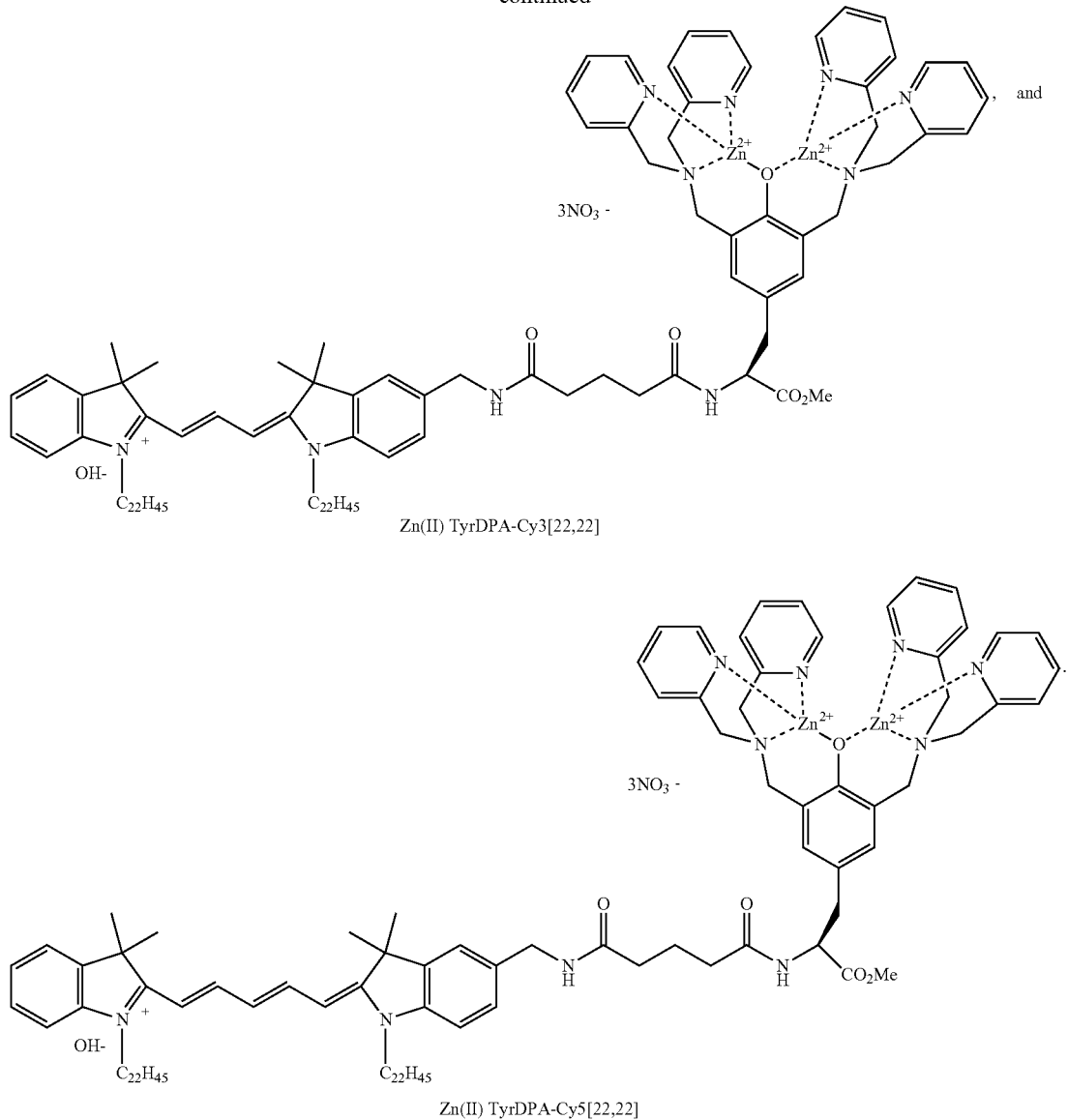
Zn(II) TyrDPA-Cy3[22,22]
Zn(II) TyrDPA-Cy5[22,22]
In one embodiment, the compound of Formula (II) is selected from the group consisting of
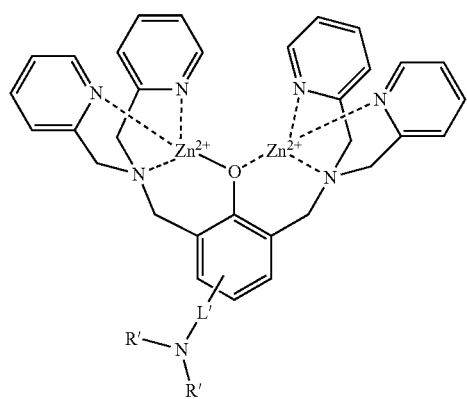
and
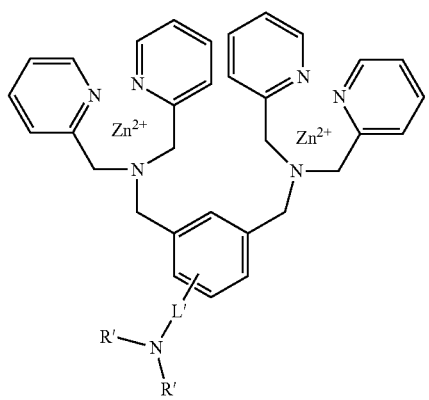
-continued
In one embodiment, the compound of Formula (II) is selected from the group consisting of

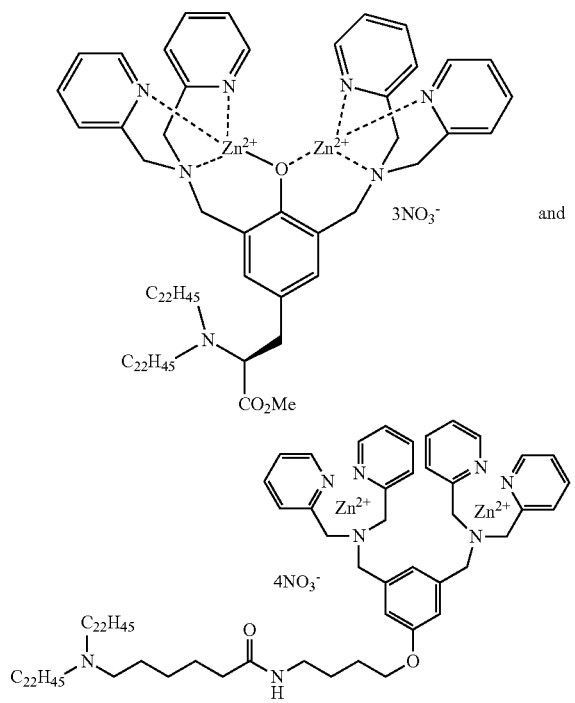

The compounds of the invention may possess one or more stereocenters, and each stereocenter may exist independently in either the R or S configuration. In one embodiment, compounds described herein are present in optically active, racemic, or meso diastereomeric forms. It is to be understood that the compounds described herein encompass racemic, optically-active, regioisomeric and stereoisomeric forms, or combinations thereof that possess the catalytically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or salts of compounds having the structure of any compound of the invention, as well as analogs of these compounds having the same type of activity. Solvates include water, ether (e.g., tetrahydrofuran, methyl tert-butyl ether, and dioxane) or alcohol (e.g., ethanol) solvates, acetates and the like. In one embodiment, the compounds described herein exist in solvated forms with solvents such as water, diethyl ether, tetrahydrofuran, dioxane, and ethanol. In another embodiment, the compounds described herein exist in unsolvated form.

In one embodiment, the compounds of the invention may exist as tautomers. All tautomers are included within the scope of the compounds presented herein.

The compounds described herein, and other related compounds having different substituents are synthesized using techniques and materials described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound described herein are modified by the use of appropriate reagents and conditions, for the introduction of the various moieties found in the formula as provided herein.

Compounds described herein are synthesized using any suitable procedures starting from compounds that are available from commercial sources.

In one embodiment, reactive functional groups, such as hydroxyl, amino, imino, thio or carboxy groups, can be protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while coexisting amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

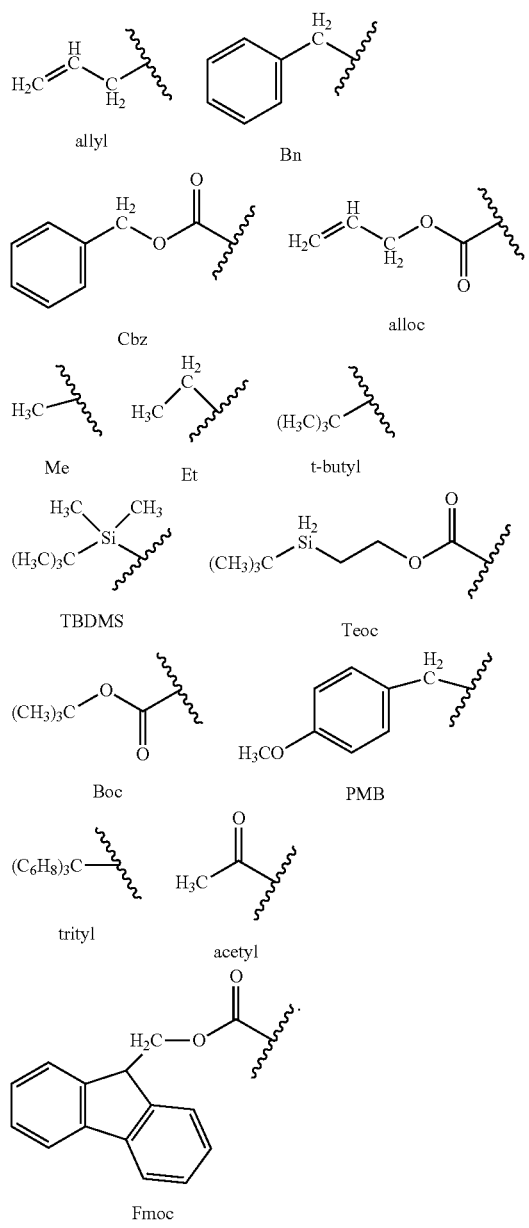

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

The compounds described herein may form salts with acids or bases, and such salts are included in the present invention. The term "salts" embraces addition salts of free acids or free basis that are useful within the methods of the invention. Salts may possess properties such as high crystallinity, which have utility in the practice of the present invention, such as for example utility in process of synthesis or purification of compounds useful within the methods of the invention.

Suitable salts may be prepared from an inorganic acid or from an organic acid. Examples of inorganic acids include perchlorate, hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, dibenzoyltartaric, dibenzyltartaric, benzoyltartaric, benzyltartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

In some embodiments, the phospholipid further comprises cholesterol. In one embodiment, the phospholipid is a phosphatidylcholine. In some exemplary embodiments, the phosphatidylcholine is selected from the group consisting of 1,2-didecanoyl-sn-glycero-3-phosphocholine (DDPC), 1,2-dierucoyl-sn-glycero-3-phosphocholine (DEPC), 1,2-dilinoleoyl-sn-glycero-3-phosphocholine (DLOPC), 1,2-dilauroyl-sn-glycero-3-phosphocholine (DLPC), 1,2-dimyristoyl-sn-glycero-3-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), egg PC (EPC), hydrogenated egg PC (HEPC), hydrogenated soy PC (HSPC), 1-myristoyl-2-palmitoyl-sn-glycero-3-phosphocholine (Milk Sphingomyelin MPPC), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), 1-stearoyl-2-palmitoyl-sn-glycero-3-phosphocholine (SPPC), and mixtures thereof.

In one embodiment, the phospholipid is a lysophosphatidylcholine. In some exemplary embodiments, the lysophosphatidylcholine phosphatidylglycerol is selected from the group consisting of 1-myristoyl-sn-glycero-3-phosphocholine, 1-palmitoyl-sn-glycero-3-phosphocholine, and 1-stearoyl-sn-glycero-3-phosphocholine.

In one embodiment, the phospholipid is a phosphatidic acid sodium salt. In some exemplary embodiments, the phosphatidic acid sodium salt is selected from the group consisting of 1,2-dierucoyl-sn-glycero-3-phosphate sodium salt (DEPA-NA), 1,2-dilauroyl-sn-glycero-3-phosphate sodium salt (DLPA-NA), 1,2-dimyristoyl-sn-glycero-3-phosphate sodium salt (DMPA-NA), 1,2-dioleoyl-sn-glycero-3-phosphate sodium salt (DOPA-NA), 1,2-dipalmitoyl-sn-glycero-3-phosphate sodium salt (DPPA-NA), 1,2-distearoyl-sn-glycero-3-phosphate sodium salt (DSPA-NA), and mixtures thereof.

In one embodiment, the phospholipid is a phosphatidylglycerol. In some exemplary embodiments, the phosphatidylglycerol is selected from the group consisting of 1,2-dierucoyl phosphatidylglycerol (DEPG), 1,2-dilauroyl phosphatidylglycerol (DLPG), 1,2-dimyristoyl phosphatidylglycerol (DMPG), 1,2-dioleoyl phosphatidylglycerol (DOPG), 1,2-dipalmitoyl phosphatidylglycerol (DPPS), 1,2- distearoyl phosphatidylglycerol (DSPG), 1-palmitoyl-2-oleoyl phosphatidylglycerol (POPG), egg phosphatidylglycerol (EPG), salts of any of the foregoing (e.g., sodium, ammonium, or sodium/ammonium), and mixtures thereof (e.g., egg phosphatidylglycerol).

In one embodiment, the phospholipid is a phosphatidylserine. In exemplary embodiments, the phosphatidylserine is selected from the group consisting of 1,2-dilauroyl-sn-glycero-3-phosphoserine sodium salt (DLPS-NA), 1,2-dimyristoyl-sn-glycero-3-phosphoserine sodium salt (DMPS-NA), 1,2-dioleoyl-sn-glycero-3-phosphoserine sodium salt (DOPS-NA), 1,2-dipalmitoyl-sn-glycero-3-phosphoserine sodium salt (DPPS-NA), 1,2-distearoyl-sn-glycero-3-phosphoserine sodium salt (DSPS-NA) and mixtures thereof.

In one embodiment, the phospholipid is a phosphatidylethanolamine. In exemplary embodiments, the phosphatidylethanolamine is selected from the group consisting of 1,2-dierucoyl-sn-glycero-3-phosphoethanolamine (DEPE), 1,2-dilauroyl-sn-glycero-3-phosphoethanolamine (DLPE), 1,2-dimyristoyl-sn-glycero-3-phosphoethanolamine (DMPE), 1,2-dioleoyl-sn-glycero-3-phosphoethanolamine (DOPE), 1,2-dipalmitoyl-sn-glycero-3-phosphoethanolamine (DPPE), 1,2-distearoyl-sn-glycero-3-phosphoethanolamine (DSPE), and 1-palmitoyl-2-oleoyl-sn-glycero-3-phosphoethanolamine (POPE) and mixtures thereof.

In various embodiments, the liposomal composition comprises a vesicle, a liposome, a nanoliposome, a niosome, a microsphere, a nanosphere, a nanoparticle, a micelle, or an exosome. In one embodiment, the liposomal composition is unilamellar. In one embodiment, the liposomal composition is multilamellar.

In one embodiment, the liposomal composition forms liposomes with an average diameter between 25 nm and 250 nm. In one embodiment, the average diameter of the liposomes is between about 50 nm and about 200 nm. In one embodiment, the average diameter is between about 100 nm and 150 nm. In one embodiment, the average diameter is about 135 nm.

In one embodiment, the polydispersity of the liposomes is between about 0.05 and about 0.25. In one embodiment, the polydispersity is between about 0.10 and 0.20. In one embodiment, the polydispersity is about 0.15.

In one embodiment, the zeta potential of the liposomes is between about +1 mV and about +5 mV. In one embodiment, the zeta potential. In one embodiment, the zeta potential of the liposomes is between about +2 mV and about +4 mV. In one embodiment, the zeta potential of the liposomes is about +3 mV.

In some embodiments of the invention, the liposomal composition further comprises an additional bioactive agent. In one embodiment, the additional bioactive agent is a chemotherapeutic agent. In one embodiment, the additional bioactive agent is an agent targeting the cardiovascular system.

Exemplary chemotherapeutic agents include, but are not limited to, cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

In one embodiment, the chemotherapeutic agent is an antiproliferative agent. Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

In one embodiment, the chemotherapeutic agent is a cytotoxic/antineoplastic agent or an anti-angiogenic agent. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

In one embodiment, the chemotherapeutic agent is selected from the group consisting of acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; bortezomib; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol;

mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In one embodiment, the liposomal composition further comprises an agent treating the cardiovascular system. In one embodiment, the agent treating the cardiovascular system is treating a congestive heart failure. In one embodiment, the agent treating congestive heart failure is an angiotensin converting enzyme (ACE) inhibitor such as benazepril, captopril, cilazapril, enalapril, fosinopril, lisinopril, moexipril, perindopril, quinapril, ramipril, trandolapril, or enalaprilat. In one embodiment, the agent treating congestive heart failure is a beta-blocker such as acebutolol, atenolol, betaxolol hydrochloride, bisoprolol fumarate, carteolol hydrochloride, carvedilol, celiprolol hydrochloride, esmolol hydrochloride, labetalol hydrochloride, levobunolol, metoprolol tartrate, metipranolol, nadolol, nebivolol, oxprenolol hydrochloride, pindolol, propranolol hydrochloride, sotalol hydrochloride, or timolol maleate. In one embodiment, the agent treating congestive heart failure is digoxin. In one embodiment, the agent treating congestive heart failure is a diuretic such as thiazide diuretic, loop diuretic, potassium-sparing diuretic, or a combination thereof. In some embodiments, thiazide diuretics include but are not limited to bendrofluazide, bendroflumethiazide, benzthiazide, chlorothiazide, chlorthalidone, cyclopenthiazide, Diucardin®, Diuril®, Enduron®, Esidrix®, Exna®, HCTZ, Hydrochlorothiazide, HydroDIURIL®, HYDROFLUMETHIAZIDE, Hydromox®, Hygroton®, indapamide, Lozol®, methyclothiazide, metolazone, Mykrox®, Naqua®, Naturetin®, Oretic®, polythiazide, quinethazone, Renese®, trichlormethiazide, xipamide, or Zaroxolyn®. In some embodiments, loop diuretics include but are not limited to furosemide/frusemide, bumetanide, or torasemide. In some embodiments, potassium-sparing diuretics include but are not limited to amiloride, triamterene, aldosterone antagonists, or spironolactone.

In one embodiment, the agent treating the cardiovascular system is an anti-arrhythmic agent. In one embodiment, the anti-arrhythmic agent is a sodium channel blocker, beta-adrenergic blocker, calcium channel blocker, or an agent that prolong repolarization. In one embodiment, sodium channel blockers include but are not limited to quinidine, procainamide, disopyramide, lidocaine, tocainide, mexiletine, encainide, or flecainide. In one embodiment, beta-adrenergic blockers include but are not limited to propranolol, acebutolol, esmolol, or sotalol. In one embodiment, agents that prolong repolarization include but are not limited to sotalol or amiodarone. In one embodiment, calcium channel blockers include but are not limited to verapamil, diltiazem, nifedipine, or mebefradil. In one embodiment, the anti-arrhythmic agent is adenosine or digoxin.

In one embodiment, the agent treating the cardiovascular system is an anti-anginal agent. In one embodiment, the anti-anginal agent is an antiplatelet agent, adrenoceptor antagonist, calcium channel blocker, or a vasodilator. In some embodiments, the adrenoceptor antagonists and calcium channel blockers comprise agents as described hereinabove. In one embodiment, the antiplatelet agent is a cyclooxygenase inhibitor, ADP inhibitor, phosphodiesterase (I) inhibitor, glycoprotein IIb/IIIa inhibitor, or an adenosine reuptake inhibitor. In one embodiment, cyclooxygenase inhibitors include but are not limited to acetylsalicylic acid or an acetylsalicylic acid in combination with dipyridimole. In one embodiment, ADP inhibitors include but are not limited to clopidogrel, CS-747, or ticlopdipine. In one embodiment, phosphodiesterase III inhibitors include but are not limited to cilostazol. In one embodiment, glycoprotein IIb/IIIa inhibitors include but are not limited to abciximab, rheopro, eptifibatide, integrilin, tirofiban, or aggrastat. In one embodiment, adenosine reuptake inhibitors include but are not limited to dipyridimole. In one embodiment, vasodilator agents include but are not limited to isosorbide dinitrate, isosorbide mononitrate, or nitroglycerine. In one embodiment, cardiac glycosides such as digitalis or ouabain may be used in combination with a SARM compound.

In one embodiment, the agent treating the cardiovascular system is a vasocative agent or an inotrope. In one embodiment, vasocative agents or inotropes include but are not limited to digoxin, dopamine, dobutamine, hydralazine, prazosin, carvedilol, nitroprusside, nitroglycerin, captopril, lisinopril, nifedipine, diltiazem, hydrochlorothiazide, furosemide, spironolactone, AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), or nitrates.

In one embodiment, the agent treating the cardiovascular system is an anticoagulant agent. In one embodiment, the anticoagulant agent is a coumarin derivative or an unfractionated heparin. In one embodiment, coumarin derivatives include but are not limited to warfarin.

In one embodiment, the agent treating the cardiovascular system is a fibrinolytic agent such as streptokinase, urokinase, alteplase, anistreplase, prourokinase, reteplase, tenecteplase, lanoteplase, staphylokinase, vampire, or alfimeprase.

In one embodiment, the agent treating the cardiovascular system is a hypercholesterolemic agent such as niacin-lovastatin, colestipol HCl, fluvastatin sodium, atorvastatin calcium, simvastatin, gemfibrozil, lovastatin, pravastatin sodium, cholestyramine, cholestyramine light, fenofibrate, colesevelam HCl, or ezetimibe.

Methods of the Invention

In one aspect, the present invention relates in part to a method of treating a platelet-related disease or disorder in a subject in need thereof, the method comprising the step of administering to the subject the liposomal composition disclosed herein. In another aspect, the present invention relates in part to a method of treating or preventing thrombosis in a subject in need thereof, the method comprising the step of administering to the subject the liposomal composition disclosed herein. In another aspect, the present invention relates in part to a method of binding phosphatidylserine, the method comprising contacting phosphatidylserine with the liposomal composition disclosed herein.

In one embodiment, the liposomal composition selectively binds to the anionic cellular membrane lipid phosphatidylserine (PS) and to PS-exposing tumor cells, resulting in PS-dependent cell killing. In one embodiment, the liposomal composition binds to PS and does not kill the cell. In one embodiment, the liposome size may affect liposome bio-distribution. In one embodiment, the PS-targeting moiety (DPA) remains sequestered in the bloodstream for a significant amount of time (on the order of hours).

In one embodiment, treatment induces mild thrombocytopenia, supporting maintenance of platelet counts within the normal range, which will further obviate bleeding diathesis that often results by generalized anti-platelet treatments. In another embodiment, the moderate effects on circulating platelet count will be transient following treatment, and rapidly recovered.

In one embodiment, the agent can be applied i.v., or topically and locally in open vascular surgical settings. In one embodiment, other clinical application methods are conceivable. Exemplary treatment applications of the methods of the invention include, but are not limited to, acute treatment for stroke, acute treatment for heart attack/myocardial infarction, acute treatment for reperfusion injury, acute anti-clotting agent in treatment of sepsis, other trauma scenarios, anti-clotting agent during surgery and for post-surgical treatment, including thrombosis resulting from bypass surgery, stent implantation, and other vascular surgical scenarios, prophylactic anti-thrombotic agent for patients at risk for thromboembolic events, including deep vein thrombosis, cancer patients, and other cases of increased risk, protection against ex vivo coagulation in platelet storage pools for apheresis/transfusion applications, and as a potent anti-inflammatory agent. In one embodiment, use of this invention will avoid bleeding complications which are prevalent problems with current anti-platelet therapies. In one embodiment, liposomes can be rather quickly cleared from circulation by the mononuclear phagocyte system on the order of hours. In one embodiment, the moderate effects on circulating platelet count are transient following treatment, and rapidly recovered. In one embodiment, treatment induces mild thrombocytopenia, supporting maintenance of platelet counts within the normal range, which will further obviate bleeding diathesis that often results by generalized anti-platelet treatments.

In one embodiment, the compositions of the invention can be used for in vivo small animal imaging research to monitor the bio-distribution of DPA-containing liposomes and to establish thrombosis models to assess spatiotemporal dynamics of liposome incorporation into thrombi and effects on thrombus stability.

In one embodiment, the compositions of the invention can be used for the preservation of inactive, intact platelets in platelet storage pools for apheresis applications, such as for hemophiliacs who require frequent platelet transfusions.

Various diseases or disorders can be treated by use of the liposomal compositions of the present invention. In one embodiment, the disease or disorder is cancer, such as, but not limited to, Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Heptatocellular Carcinoma (HCC); Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocvtoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Cell Carcinoma (RCC); Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; Wilms Tumor, and the like.

The methods of treatment of the invention include various administration methods, such as for example parenteral administration. As used herein, "parenteral administration" of a composition of the invention includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, bolus injections, and kidney dialytic infusion techniques. In one embodiment, parenteral administration includes depositing the micro-beads of the invention, or a composition comprising the micro-beads of the present invention, into an artery of a subject.

Pharmaceutical Compositions

Also provided herein are pharmaceutical compositions comprising liposomal compositions of the present invention. The pharmaceutical compositions may be suitable for a variety of modes of administration described herein, including for example systemic or localized administration. The pharmaceutical compositions can be in the form of eye drops, injectable solutions, or in a form suitable for inhalation (either through the mouth or the nose) or oral administration. The pharmaceutical compositions described herein can be packaged in single unit dosages or in multidosage forms.

In some embodiments, the pharmaceutical compositions comprise a pharmaceutically acceptable carrier suitable for administration to human. In some embodiments, the pharmaceutical compositions comprise a pharmaceutically acceptable carrier suitable for intraocular injection. In some embodiments, the pharmaceutical compositions comprise a pharmaceutically acceptable carrier suitable for topical application. In some embodiments, the pharmaceutical compositions comprise a pharmaceutically acceptable carrier suitable for intravenous injection. In some embodiments, the pharmaceutical compositions comprise and a pharmaceutically acceptable carrier suitable for injection into the arteries.

The pharmaceutical compositions are generally formulated as sterile, substantially isotonic, and in full compliance with all Good Manufacturing Practice (GMP) regulations of the U.S. Food and Drug Administration. In some embodiments, the composition is free of pathogen. For injection, the pharmaceutical composition can be in the form of liquid solutions, for example in physiologically compatible buffers such as Hank's solution or Ringer's solution. In addition, the pharmaceutical composition can be in a solid form and redissolved or suspended immediately prior to use. Lyophilized compositions are also included.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

The present invention in some embodiments provides compositions comprising liposomal compositions and a pharmaceutically acceptable carrier suitable for administration to the eye. Such pharmaceutical carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. Suitable pharmaceutical excipients include starch, glucose, lactose, sucrose, gelatin, malt, rice, sodium state, glycerol monostearate, glycerol, propylene, water, and the like. The pharmaceutical composition, if desired, can also contain minor amounts of wetting or emulsifying agents, or pH buffering agents. The liposomal compositions and other components of the composition may be encased in polymers or fibrin glues to provide controlled release of the molecule. These compositions can take the form of solutions, suspensions, emulsions, ointment, gel, or other solid or semisolid compositions, and the like. The pharmaceutical compositions typically have a pH in the range of 4.5 to 8.0. The compositions must also be formulated to have osmotic values that are compatible with the aqueous humor of the eye and ophthalmic tissues. Such osmotic values will generally be in the range of from about 200 to about 400 milliosmoles per kilogram of water ("mOsm/kg"), but will preferably be about 300 mOsm/kg.

In some embodiments, the pharmaceutical composition is formulated in accordance with routine procedures as a pharmaceutical composition adapted for injection intravenously, intraperitoneally, or intravitreally. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions may further comprise additional ingredients, for example preservatives, buffers, tonicity agents, antioxidants and stabilizers, nonionic wetting or clarifying agents, viscosity-increasing agents, and the like.

Suitable preservatives for use in a solution include polyquaternium-1, benzalkonium chloride, thimerosal, chlorobutanol, methyl paraben, propyl paraben, phenylethyl alcohol, edetate disodium, sorbic acid, benzethonium chloride, and the like. Typically (but not necessarily), such preservatives are employed at a level of from 0.001% to 1.0% by weight.

Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5.

Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

The use of viscosity enhancing agents to provide topical compositions with viscosities greater than the viscosity of simple aqueous solutions may be desirable. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents know to those skilled in the art. Such agents are typically employed at a level of from 0.01% to 2% by weight.

In some embodiments, there is provided a pharmaceutical composition for delivery of a nucleotide encapsulated in a liposomal composition. The pharmaceutical composition for gene therapy can be in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical composition can comprise one or more cells which produce the gene delivery system.

In clinical settings, a gene delivery system for a gene therapeutic can be introduced into a subject by any of a number of methods. For instance, a pharmaceutical composition of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter, See U.S. Pat. No. 5,328,470, or by stereotactic injection, Chen et al. (1994), Proc. Natl. Acad. Sci., USA 91: 3054-3057.

Administration

The compositions described herein can be administered to an individual via any route, including, but not limited to, intravenous (e.g., by infusion pumps), intraperitoneal, intraocular, intra-arterial, intrapulmonary, oral, intravesicular, intramuscular, intra-tracheal, subcutaneous, intrathecal, transdermal, transpleural, topical, inhalational (e.g., as mists of sprays dry powders, or aerosols), mucosal (such as via nasal mucosa), gastrointestinal, intraarticular, intracisternal, intraventricular, rectal (i.e., via suppository), vaginal (i.e., via pessary), intracranial, intraurethral, intrahepatic, and intratumoral. In some embodiments, the compositions are administered systemically (for example by intravenous injection). In some embodiments, the compositions are administered locally (for example by intraarterial or intraocular injection). In some embodiments, the compositions are administered by ex vivo incubation or perfusion.

Dosing

The optimal effective amount of the compositions can be determined empirically and will depend on the type and severity of the disease, route of administration, disease progression and health, mass and body area of the individual. Such determinations are within the skill of one in the art. The effective amount can also be determined based on in vitro complement activation assays. Examples of dosages of drug delivery particles which can be used for methods described herein include, but are not limited to, an effective amount within the dosage range of any of about 0.01 mg/kg to about 300 mg/kg, or within about 0.1 mg/kg to about 40 mg/kg, or with about 1 mg/kg to about 20 mg/kg, or within about 1 mg/kg to about 10 mg/kg. In some embodiments, the amount of biologically active agent administered to an individual is about 10 mg to about 500 mg per dose, including for example any of about 10 mg to about 50 mg, about 50 mg to about 100 mg, about 100 mg to about 200 mg, about 200 mg to about 300 mg, about 300 mg to about 500 mg, about 500 mg to about 1 mg, about 1 mg to about 10 mg, about 10 mg to about 50 mg, about 50 mg to about 100 mg, about 100 mg to about 200 mg, about 200 mg to about 300 mg, about 300 mg to about 400 mg, or about 400 mg to about 500 mg per dose.

The pharmaceutical compositions comprising liposomal compositions may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The drug delivery particles may be administered by injection or surgical implantation in various locations.

Dosage amounts and frequency will vary according the particular formulation, the dosage form, and individual patient characteristics. Generally speaking, determining the dosage amount and frequency for a particular formulation, dosage form, and individual patient characteristic can be accomplished using conventional dosing studies, coupled with appropriate diagnostics.

Combination Therapy

In some embodiments, provided pharmaceutical formulations are administered to a subject in combination with one or more other therapeutic agents or modalities, for example, useful in the treatment of one or more diseases, disorders, or conditions treated by the relevant provided pharmaceutical formulation, so the subject is simultaneously exposed to both.

The particular combination of therapies (substances and/or procedures) to employ in a combination regimen will take into account compatibility of the desired substances and/or procedures and the desired therapeutic effect to be achieved. In some embodiments, provided compositions can be administered concurrently with, prior to, or subsequent to, one or more other therapeutic agents (e.g., desired known antimycobacterial therapeutics).

It will be appreciated that the therapies employed may achieve a desired effect for the same disorder (for example, a therapeutic compound useful for mycobacterial infections administered concurrently with a composition of the present invention), or they may achieve different effects (for example, a composition of the present invention may be administered concurrently with a therapeutic agent that is useful for alleviating adverse side effects, for instance, fever, pain, nausea, etc.). In some embodiments, the composition of the present invention are administered with a second therapeutic agent.

As used herein, the terms "in combination with" and "in conjunction with" mean that the drug delivery particles of the present invention can be administered concurrently with, prior to, or subsequent to, one or more other desired therapeutics such as an analgesic, antibacterial, antiviral, anticancer, or biologic agent including but not limited to a sub-therapeutic dose of such an agent. In general, each substance will be administered at a dose and/or on a time schedule determined for that agent.

In certain embodiments, the method comprises administering a composition comprising a combination of an antibacterial agent and the drug delivery particles described herein.

In certain embodiments, the method comprises administering one or more compositions. For example, in one embodiment, the method comprises administering a first composition comprising an antibacterial agent and a second composition comprising the liposomal compositions described herein. The different compositions may be administered to the subject in any order and in any suitable interval. For example, in certain embodiments, the one or more compositions are administered simultaneously or near simultaneously. In certain embodiments, the method comprises a staggered administration of the one or more compositions, where a first composition is administered and a second composition administered at some later time point. Any suitable interval of administration which produces the desired therapeutic effect may be used.

In certain embodiments, the method has an additive effect, wherein the overall effect of the administering a combination of therapeutic agents or procedures is approximately equal to the sum of the effects of administering each therapeutic agent or procedure alone. In other embodiments, the method has a synergistic effect, wherein the overall effect of administering a combination of therapeutic agents or procedures is greater than the sum of the effects of administering each therapeutic agent or procedure alone.

Unit Dosages, Articles of Manufacture, and Kits

Also provided are unit dosage forms of drug delivery particle compositions, each dosage containing from about 0.01 mg to about 50 mg, including for example any of about 0.1 mg to about 50 mg, about 1 mg to about 50 mg, about 5 mg to about 40 mg, about 10 mg to about 20 mg, or about 15 mg of the biologically active agent. In some embodiments, the unit dosage forms of drug delivery particles comprise about any of 0.01 mg-0.1 mg, 0.1 mg-0.2 mg, 0.2 mg-0.25 mg, 0.25 mg-0.3 mg, 0.3 mg-0.35 mg, 0.35 mg-0.4 mg, 0.4 mg-0.5 mg, 0.5 mg-1.0 mg, 10 mg-20 mg, 20 mg-50 mg, 50 mg-80 mg, 80 mg-100 mg, 100 mg-150 mg, 150 mg-200 mg, 200 mg-250 mg, 250 mg-300 mg, 300 mg-400 mg, or 400 mg-500 mg biologically active agent. The term "unit dosage form" refers to a physically discrete unit suitable as unitary dosages for an individual, each unit containing a predetermined quantity of active material calculated to produce the desired therapeutic effect, in association with a suitable pharmaceutical carrier, diluent, or excipient. These unit dosage forms can be stored in suitable packaging in single or multiple unit dosages and may also be further sterilized and sealed.

The present invention also provides kits comprising compositions (or unit dosages forms and/or articles of manufacture) described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

DPA-containing liposomes have been explored as carriers for anti-tumor use (*Molecular Pharmaceutics* (2017) 14, 147-156) but not as carriers of anti-thrombotics. Thrombin-targeted anti-coagulation liposomes have previously been reported in the literature (e.g., Endreas et al. (2016) ChemMedChem 11, 340-349; Palekar et al. (2013) Mol. Pharm. 10, 4168-4175); however, these liposomes did not prevent injury-induced vessel occlusion, and the liposomes were not based on DPA-phosphatidylserine (PS) or DPA-platelet interactions. The liposome size and composition in this invention ensure that the PS-targeting moiety (DPA) remains sequestered in the bloodstream for a significant amount of time (on the order of hours), whereas small molecule PS-targeting non-liposomal drugs may cross the vessel wall and have adverse effects. The invention has several additional major advantages over existing alternatives.

By only binding to and disrupting activated platelets, use of this invention will avoid bleeding complications which are prevalent problems with current anti-platelet therapies. Treatment induces mild thrombocytopenia, supporting maintenance of platelet counts within the normal range, which will further obviate bleeding diathesis that often results by generalized anti-platelet treatments. Also due to the likely rapid clearance of the agent (see below), the moderate effects on circulating platelet count are transient following treatment, and rapidly recovered. The agent can be applied i.v., or topically and locally in open vascular surgical settings. Other clinical application methods are conceivable. Liposomes can be rather quickly cleared from circulation by the mononuclear phagocyte system on the order of hours. Thus, unlike current anti-coagulants, this product exerts only acute anti-thrombotic effect, no long-term side effects. The preservation of inactive, intact platelets for apheresis applications, such as for hemophiliacs who require frequent platelet transfusions, has been an unsolved clinical problem for decades. This invention may be useful to help preserve stored platelets for such applications Current anti-coagulants used clinically, primarily warfarin and heparin, have major clinical problems. Heparin treatment can cause heparin-induced thrombocytopenia as a result of antibodies against heparin-platelet factor 4 complexes, and warfarin treatment is well known to cause bleeding by globally inhibiting synthesis of essential clotting factors. Both of these complications can have serious immediate consequences but also cause long-term problems. Newer anti-coagulant drugs targeting coagulation factors, e.g. factor Xa inhibitors such as Xarelto (rivaroxaban), apixaban, edoxaban, and Pradaxa (dabigatran), have quick onset of action, but short half-lives, and require substantial dosage for acute effects. Such effects are avoided with this invention. Together these represent major advantages with this invention over current modalities.

Figure 5:
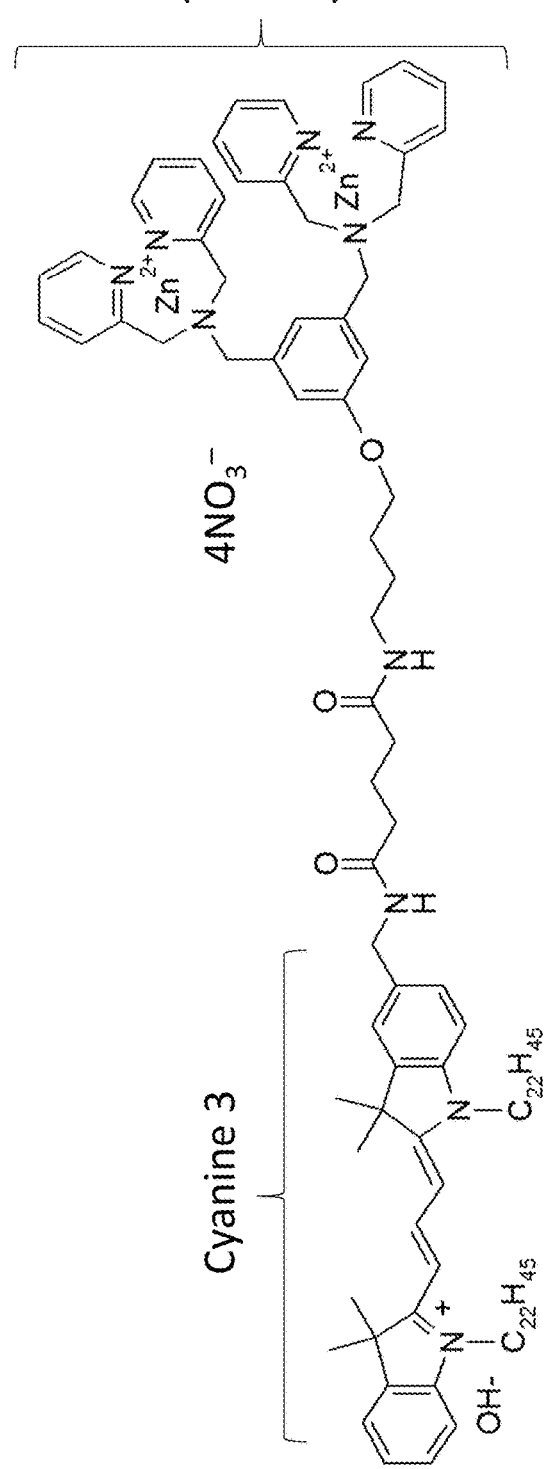
FIG. 5, depicts the chemical structures of exemplary compound Zn (II) DPA-Cy3 [22,22] and Compound 2.
Figure 5:
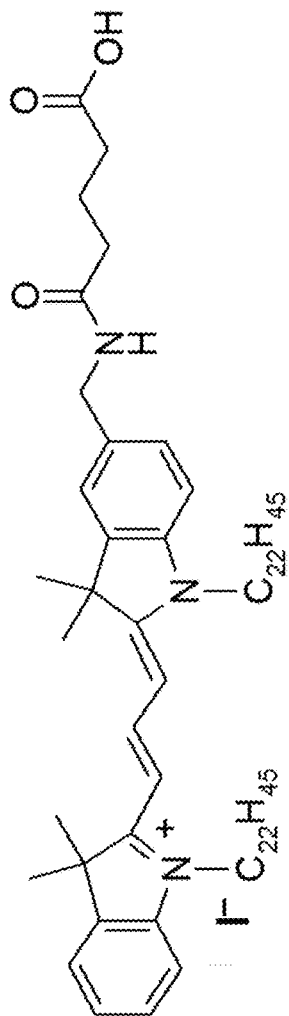
Figure 6:
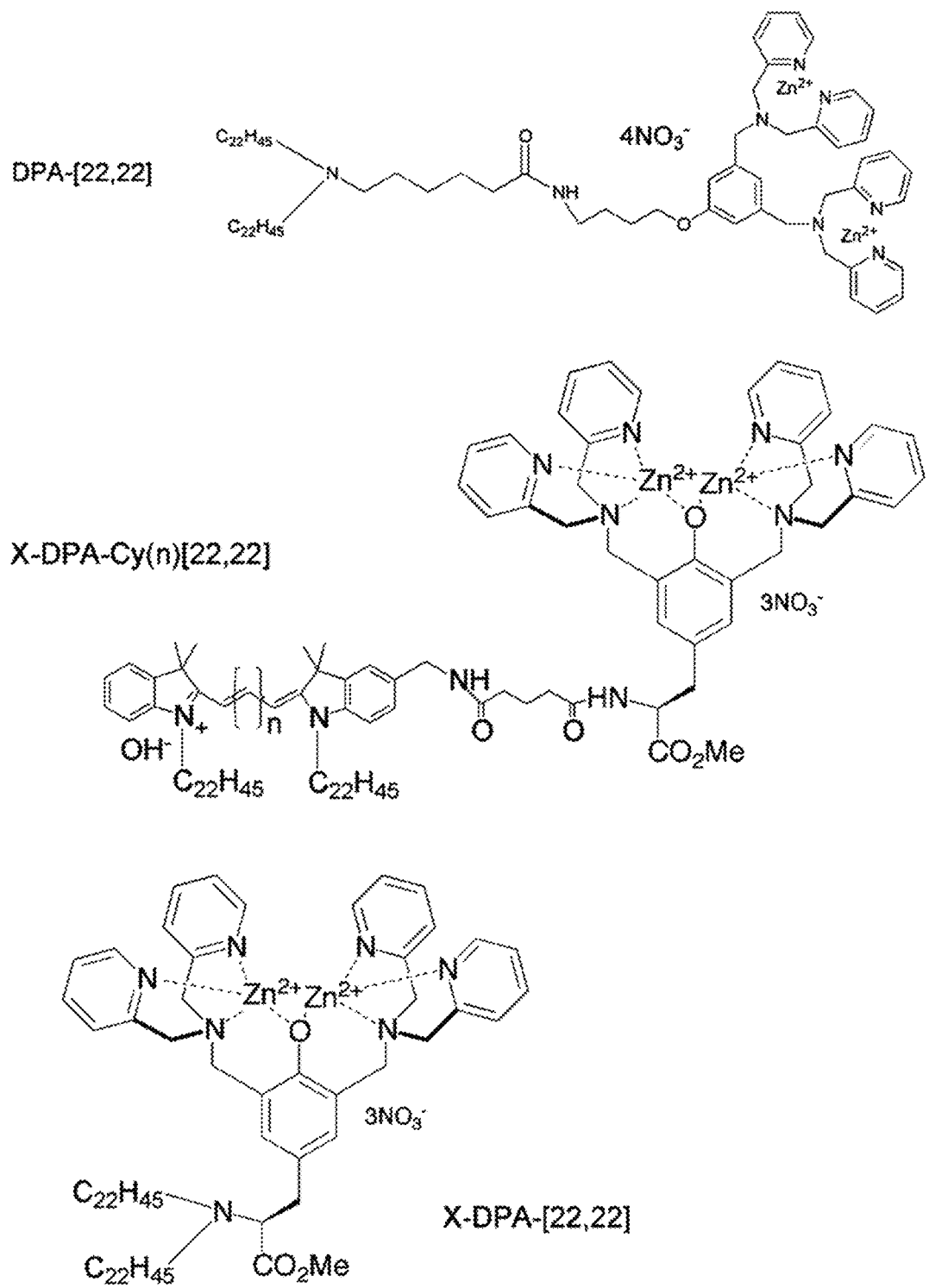
FIG. 6, depicts the chemical structures of exemplary compounds DPA-[22.22], X-DPA-Cy(n)[22,22], and X-DPA-[22,22].

In these studies, DPA liposomes (DPA-Cy3 [22,22]/POPC) were used and control liposomes in which DPA is substituted with Compound 2 (FIG. 5), an inert non-PS-binding Cy3 analog, as well as liposomes with no Cy3 nor DPA (POPC), from the previous published study (Mol Pharm. 2017 Jan. 3; 14(1):147-156).

Example 1: DPA Liposomes Selectively Bind Activated Platelets In Vitro

Direct binding of activated platelets was tested ex vivo, to DPA-loaded liposomes and Comp2-loaded control liposomes, both of which include a Cy3 fluorophore as part of the chemical structure, which allow for laser tracking of the liposomes. $2\times10^8$ human platelets isolated from freshly drawn anti-coagulated blood (citrate as anti-coagulant) were mixed with 5 μl of either liposome formulation, then immediately treated with platelet agonists with no stirring and incubated at 37° C. for 10 min, fixed, washed and analyzed for Cy3 fluorescence by flow cytometry. As shown in FIG. 1, stimulation with either thrombin PAR agonist or 2Me-SADP P2Y receptor agonist resulted in binding of DPA liposomes but not Comp2 liposomes to platelets. Binding is <100% because the assay requires no stirring upon agonist stimulation to prevent platelet aggregation; hence, only ~50% of the platelets are exposed to the given agonist. However, addition of 2 mM $MnCl_2$ to the buffer, which alters the membrane composition of all the platelets including induction of PS exposure, resulted in 100% of the platelets binding the DPA liposomes, but very little Comp2 liposome binding was evident. Thus, DPA liposomes selectively and rapidly bind to the surface of acutely activated platelets in vitro.

Example 2: Mild Thrombocytopenia by DPA Liposome Transfusion

Figure 2:
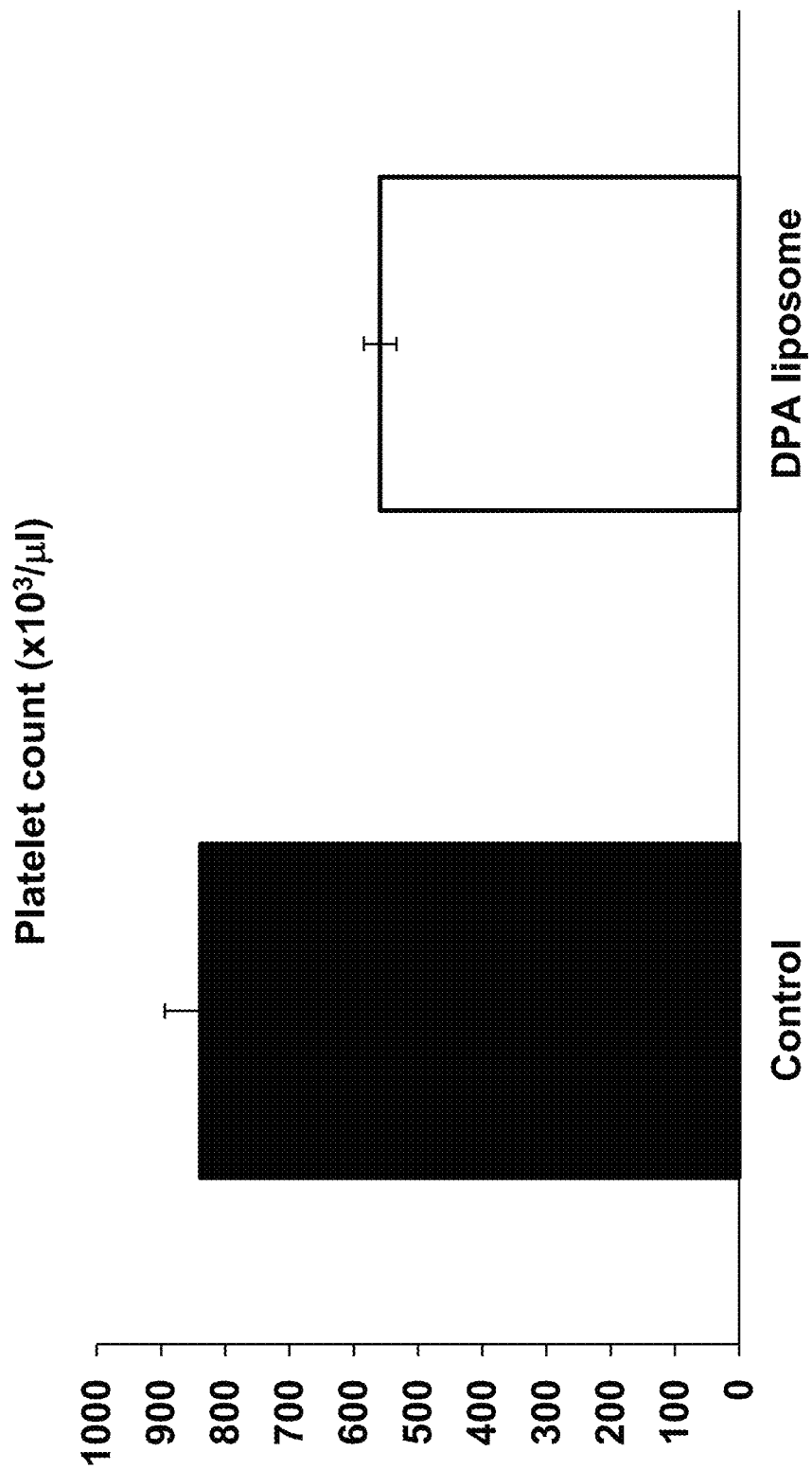
FIG. 2, depicts the results of example experiment demonstrating DPA-Cy3 liposomes induce mild thrombocytopenia in normal WT mice. Mice were transfused with liposomes as indicated and blood cell counts analyzed after 24 hrs, shown ±s.e.m. n=3.

Platelet counts were assessed by HEMAVET analysis of mouse whole blood, 24 hours after i.v. transfusion of 200 μl of DPA or POPC (control) liposomes in the mouse tail vein. No changes to RBCs or WBCs were evident (not shown). DPA liposome transfusion was associated with ~30% decrease in circulating platelets (FIG. 2). This reduction in platelets likely represents clearance of platelets with homeostatic low levels of exposed PS, and indicates that DPA liposomes do not reduce platelet counts below a normal range.

Example 3: DPA Liposomes Cause Prolonged Prothrombin Time

Figure 3:
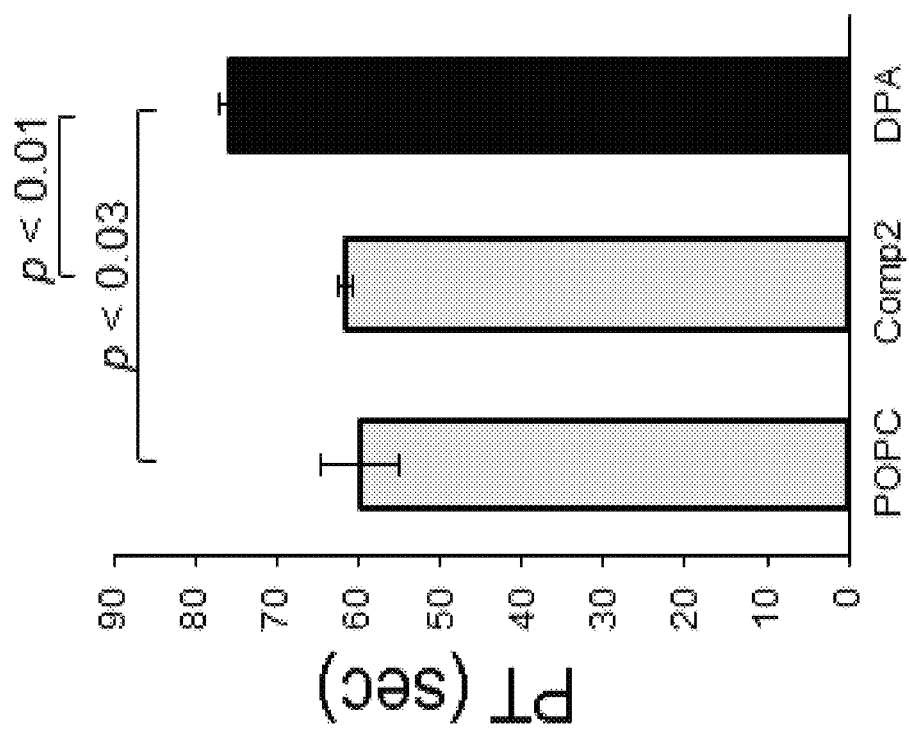
FIG. 3, depicts the results of example experiment demonstrating DPA-Cy3 liposomes cause prolonged pro-thrombin time (PT). Dilute pro-thrombin time was measured in the presence of DPA and control liposomes using platelet-poor plasma, recombinant Tissue Factor/FVIIa and phospholipids by standard methods. Shown are PT mean±s.e.m. n=3.

It was hypothesized that DPA liposomes may block thrombosis by interfering with coagulation proteins anchored to surface PS. Blockade of PS should have the effects of inhibiting PS-dependent coagulation proteins including Tissue Factor (Factor III), which cleaves pro-thrombin to generate active thrombin, which in turn causes fibrinolysis supporting platelet aggregation and thrombus formation. Significant inhibition of pro-thrombin time (PT) in the presence of DPA liposomes in vitro was observed (FIG. 3), indicating a direct role for DPA liposomes in interfering with the extrinsic coagulation pathway. Since in this in vitro assay, PT is driven by PS-mediated Tissue Factor activation, these data support the hypothesis that DPA liposomes selectively interfere with PS-dependent coagulation.

Example 4: DPA Liposomes Block Induced Pulmonary Thromboembolism in Mice

Figure 4:
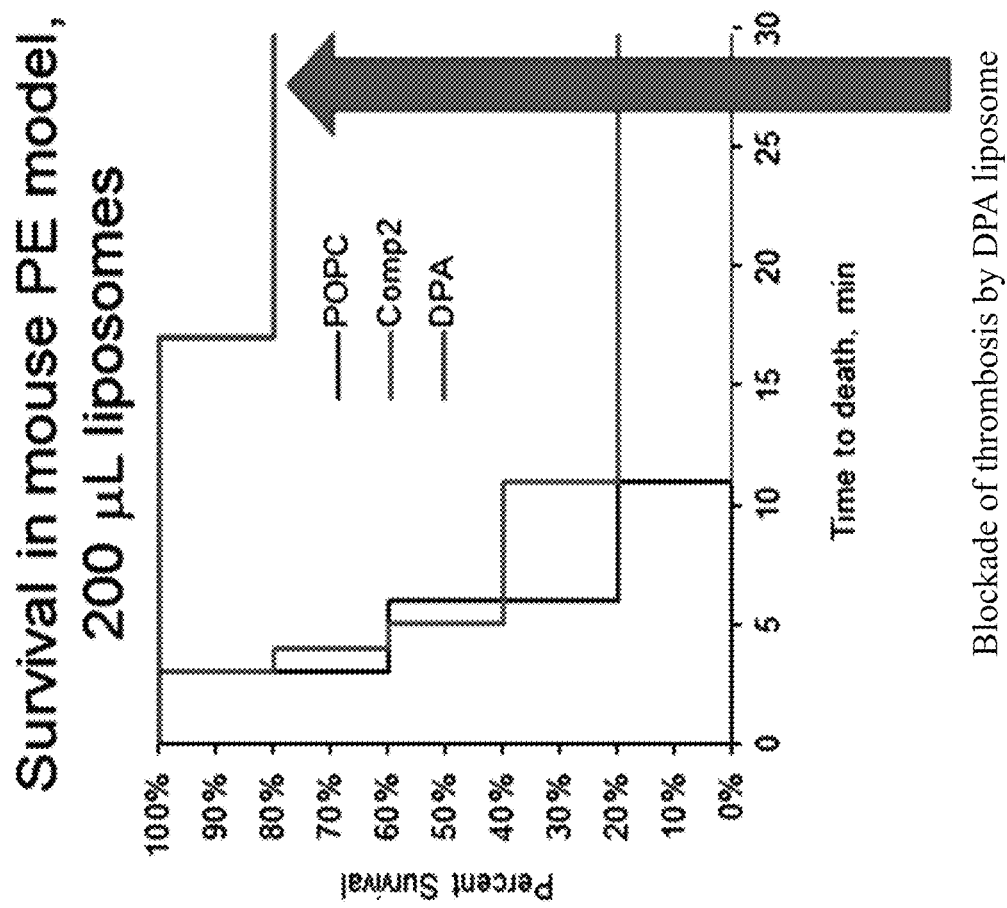
FIG. 4, depicts the results of example experiment demonstrating DPA-Cy3 liposomes prevent occlusive thrombosis. WT mice were transfused with the indicated liposomes and given collagen/epinephrine to induce pulmonary embolism. Survival times were collected by monitoring time to cessation of breathing. n=5 each.

The standard collagen/epinephrine pulmonary embolism (PE) model of survival was employed to investigate potential anti-thrombotic effects of DPA liposomes. Mice were transfused with 200 µl of either DPA, Comp2, or POPC liposomes 15 minutes prior to retroorbital injection of collagen/epinephrine, which causes acute platelet activation resulting in arterial thrombosis not associated with damaged vessel walls, creating an immediate thromboembolism which clogs the pulmonary artery, resulting in death under anesthesia. This assay is commonly used to test efficacies of anti-thrombotic treatments, as prolonged survival requires potent anti-platelet effects of the given treatment to prevent arterial occlusion. Whereas mice expired within a few minutes in the presence of POPC or Comp2 liposomes (n=5), DPA liposome-transfused mice showed no signs of PE and survived through the 30-minute experimental time frame, with the exception of one animal which died at 17 minutes (FIG. 4). Surviving animals were sacrificed and Evans blue dye was injected through the right ventricle to assay for PE directly. Mice which died during the experimental time frame showed unstained lungs, demonstrating occlusive PE, whereas DPA liposome-transfused mice had blue lungs, demonstrating perfusion of dye from the heart and lack of PE (not shown). Thus, DPA liposomes directly and potently prevented pulmonary embolism in a model of platelet-mediated thrombosis in vivo.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:
1. An anti-thrombolytic liposomal composition comprising:
 a phospholipid; and
 a compound of Formula (I);

FD-L-MBD        Formula (I);

wherein, in Formula (I), FD is a fluorescent domain which further comprises at least one hydrophobic group;
L is a divalent linker; and
MBD is a metal-binding domain.

2. The liposomal composition of claim 1, wherein FD is represented by the following Formula (III):

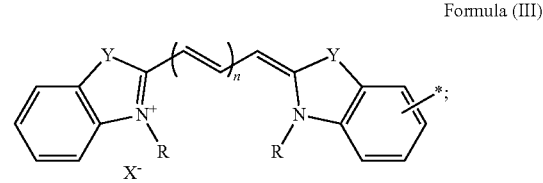

Formula (III)

wherein Y is O, S, Si(Me)$_2$, or C(Me$_2$);
X is OH, Cl, I, Br, F, ClO$_4$, NO$_3$, or CH$_3$C(O)O;
n is an integer selected from the group consisting of 1, 2, and 3;
each of occurrence of R may be the same or different and represents a linear or branched (C$_1$-C$_{40}$)alkyl group; and
* represents the connection to divalent linking group L.

3. The liposomal composition of claim 2, wherein R is a linear (C-$_{10}$-C$_{28}$)alkyl group.

4. The liposomal composition of claim 1, wherein MBD comprises Cu$^{2+}$, Cu$^+$, or Zn$^{2+}$.

5. The liposomal composition of claim 1, wherein MBD comprises Zn$^{2+}$.

6. The liposomal composition of claim 1, wherein MBD comprises di-(2-picolyl)amine.

7. The liposomal composition of claim 2, wherein the compound of Formula (I) is

8. The liposomal composition of claim 1, wherein the compound of Formula (I) is selected from the group consisting of:

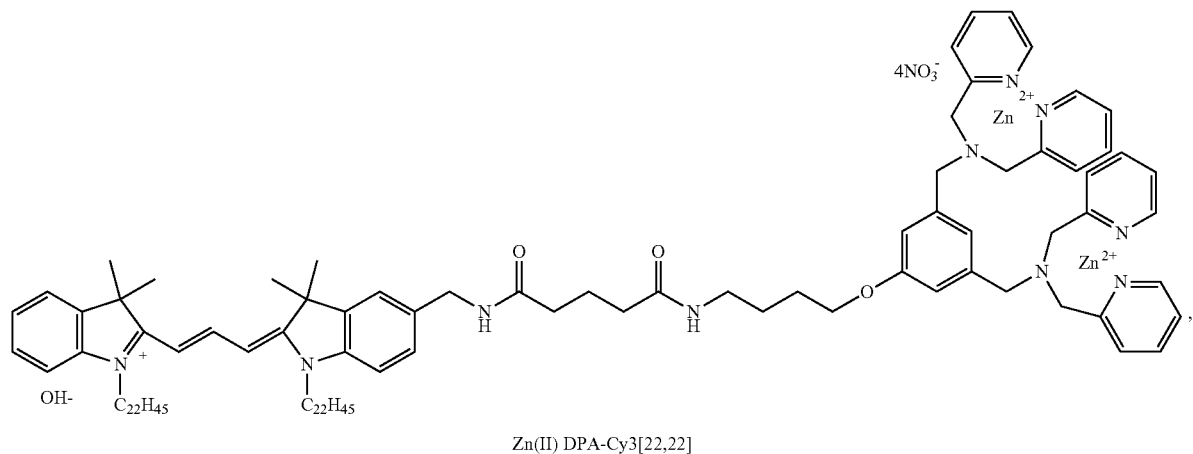
Zn(II) DPA-Cy3[22,22]
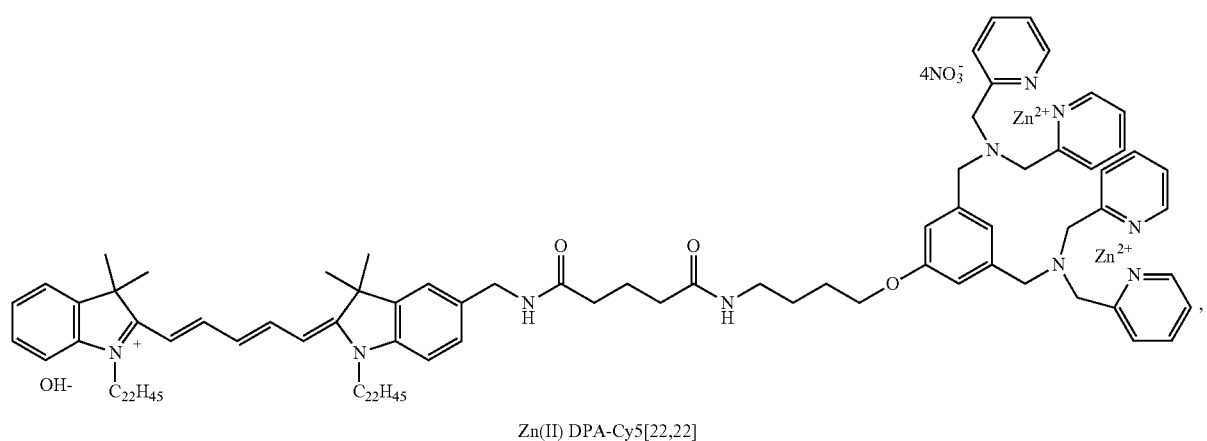
Zn(II) DPA-Cy5[22,22]
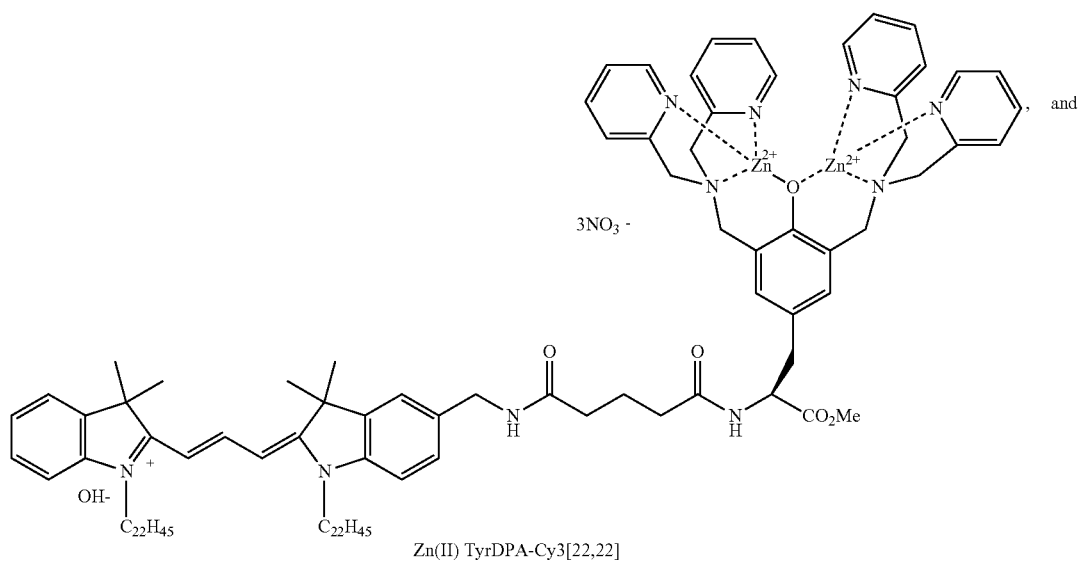
Zn(II) TyrDPA-Cy3[22,22]

-continued

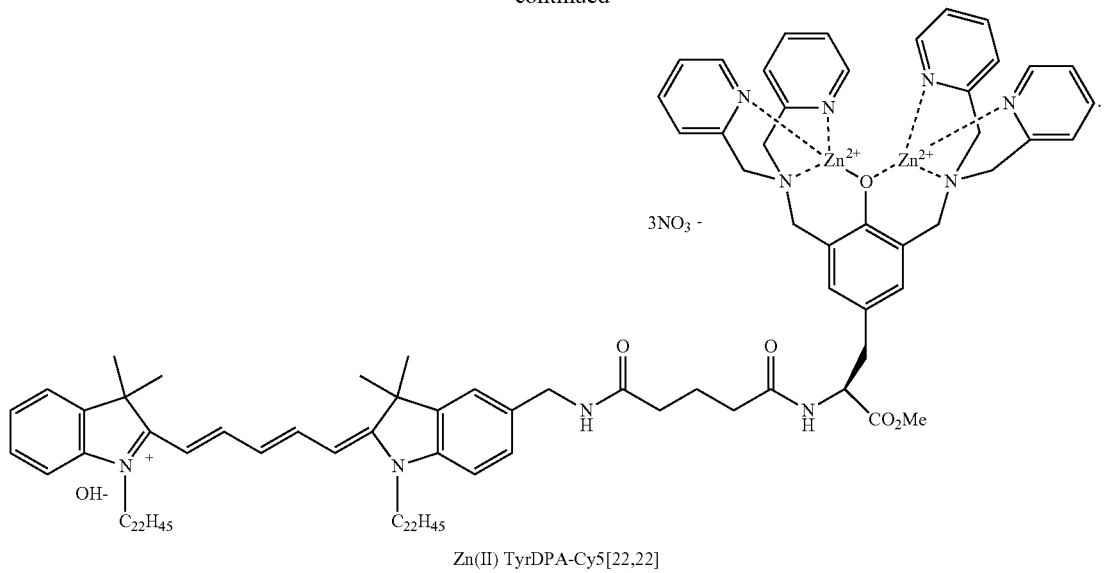

Zn(II) TyrDPA-Cy5[22,22]

9. An anti-thrombolytic liposomal composition comprising:
   a phospholipid; and
   a compound of Formula (II);

(R')$_2$N-L'-MBD'    Formula (II);

wherein, in Formula (II), R' is a linear or branched (C$_3$-C$_{28}$) alkyl group;
   L' is a divalent linker; and
   MBD' is a metal-binding domain.

10. The liposomal composition of claim 9, wherein the compound of Formula (II) is selected from the group consisting of

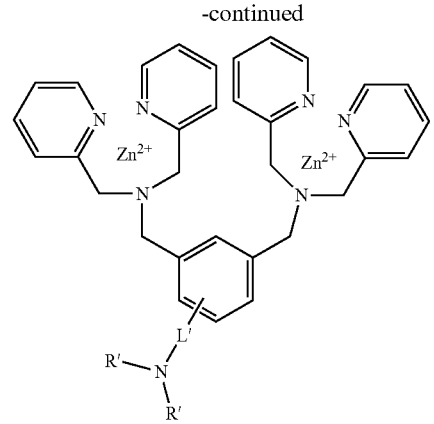

11. The liposomal composition of claim 9, wherein the compound of Formula (II) is selected from the group consisting of

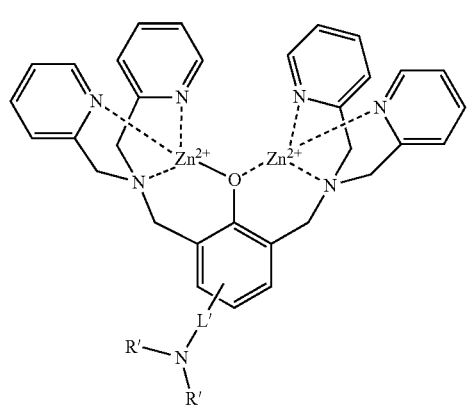

and

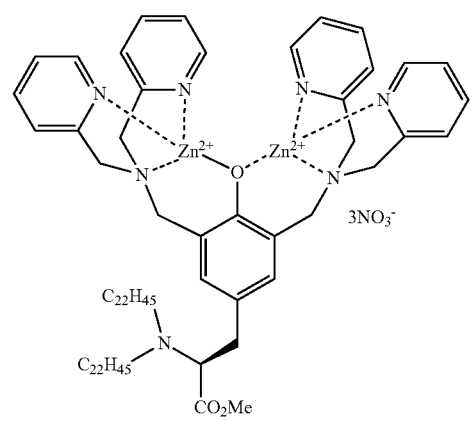

and

-continued

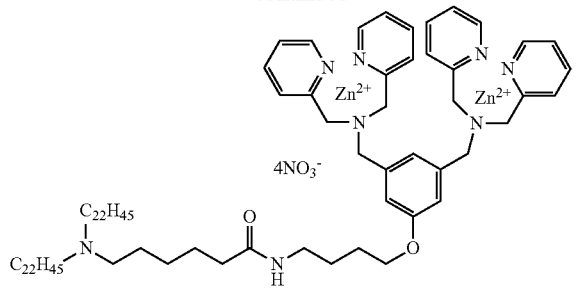

12. The liposomal composition of claim 1, wherein the phospholipid is selected from the group consisting of a phosphatidylcholine, a lysophosphatidylcholine, a phosphatidic acid sodium salt, a phosphatidylglycerol, a phosphatidylserine, and a phosphatidylethanolamine.

13. The liposomal composition of claim 1, wherein the phospholipid is selected from the group consisting of 1,2-dipalmitoyl-sn-glycero-3-phosphocholine (DPPC), 1,2-dioleoyl-sn-glycero-3-phosphocholine (DOPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-palmitoyl-sn-glycero-3-phosphocholine (SPPC), and 1-myristoyl-2-palmitoyl-sn-glycero-3-phosphocholine (MPPC).

14. The liposomal composition of claim 1, wherein the phospholipid forms a vesicle selected from the group consisting of a liposome, a nanoliposome, a niosome, a microsphere, a nanosphere, a nanoparticle, a micelle, and an exosome.

15. The liposomal composition of claim 14, wherein the phospholipd forms a liposome with average diameter of between about 100 nm and 150 nm.

16. The liposomal composition of claim 14, wherein the vesicle is unilamellar.

17. The liposomal composition of claim 1, further comprising a chemotherapeutic agent.

18. The liposomal composition of claim 1, further comprising an antiplatelet agent, an adrenoceptor antagonist, a calcium channel blocker, or a vasodilator.

19. A method of treating a platelet-related disease or disorder in a subject in need thereof, the method comprising the step of administering to the subject the liposomal composition of claim 1.

20. The method of claim 19, wherein the platelet-related disease or disorder is selected from the group consisting of stroke, myocardial infarction, reperfusion injury, sepsis, clotting during surgery, deep vein thrombosis, thrombosis resulting from bypass surgery, stent implantation, and inflammation.

21. A method of treating or preventing thrombosis in a subject in need thereof, the method comprising the step of administering to the subject the liposomal composition of claim 1.

22. A method of binding phosphatidylserine, the method comprising contacting phosphatidylserine with the liposomal composition of claim 1.

23. A method of treating a platelet-related disease or disorder in a subject in need thereof, the method comprising the step of administering to the subject the liposomal composition of claim 9.

* * * * *